United States Patent
Amendt et al.

(10) Patent No.: US 10,519,443 B2
(45) Date of Patent: Dec. 31, 2019

(54) MICRORNA INHIBITOR SYSTEM AND METHODS OF USE THEREOF

(71) Applicant: UNIVERSITY OF IOWA RESEARCH FOUNDATION, Iowa City, IA (US)

(72) Inventors: Brad A. Amendt, Iowa City, IA (US); Huojun Cao, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/508,857

(22) PCT Filed: Sep. 8, 2015

(86) PCT No.: PCT/US2015/048986
§ 371 (c)(1),
(2) Date: Mar. 3, 2017

(87) PCT Pub. No.: WO2016/040347
PCT Pub. Date: Mar. 17, 2016

(65) Prior Publication Data
US 2017/0306326 A1    Oct. 26, 2017

Related U.S. Application Data

(60) Provisional application No. 62/047,390, filed on Sep. 8, 2014.

(51) Int. Cl.
C07H 21/04 (2006.01)
C12N 15/113 (2010.01)
C12N 15/11 (2006.01)

(52) U.S. Cl.
CPC .......... *C12N 15/113* (2013.01); *C12N 15/111* (2013.01); *C12N 2310/113* (2013.01); *C12N 2310/531* (2013.01); *C12N 2330/51* (2013.01)

(58) Field of Classification Search
None
See application file for complete search history.

(56) References Cited

U.S. PATENT DOCUMENTS

| | | |
|---|---|---|
| 4,962,091 A | 10/1990 | Eppstein et al. |
| 5,252,701 A | 10/1993 | Jarrett et al. |
| 5,350,674 A | 9/1994 | Boenisch et al. |
| 5,585,362 A | 12/1996 | Schwarz et al. |
| 5,980,948 A | 11/1999 | Goedemoed et al. |
| 6,153,212 A | 11/2000 | Mao et al. |
| 6,322,797 B1 | 11/2001 | Mao et al. |
| 6,419,709 B1 | 7/2002 | Mao et al. |
| 6,485,737 B1 | 11/2002 | Mao et al. |
| 6,503,538 B1 | 1/2003 | Chu et al. |
| 6,583,219 B2 | 6/2003 | Won et al. |
| 6,592,895 B2 | 7/2003 | Lang et al. |
| 6,600,010 B2 | 7/2003 | Mao et al. |

FOREIGN PATENT DOCUMENTS

| | | |
|---|---|---|
| EP | 2363467 A1 | 9/2011 |
| EP | 2502997 A1 | 9/2012 |
| WO | 1994007529 A1 | 4/1994 |
| WO | 2006133022 A2 | 12/2006 |
| WO | 2007095387 A2 | 8/2007 |
| WO | 2007109131 A2 | 9/2007 |
| WO | 2008150897 A2 | 12/2008 |
| WO | 2011133874 A1 | 10/2011 |

OTHER PUBLICATIONS

Zhu, et al., "Sponge Transgenic Mouse Model Reveals Important Roles for the MicroRNA-183 (miR-183)/96/182 Cluster in Postmitotic Photoreceptors of the Retina", J Biol Chem 286, 31749-31760 (2011).
Ambros, "The functions of animal microRNAs", Nature 431, 350-355 (2004).
Bartel, "MicroRNAs: genomics, biogenesis, mechanism, and function", Cell 116, 281-297 (2004).
Bartel, "MicroRNAs: target recognition and regulatory functions", Cell 136, 215-233 (2009).
Bartels, et al., "MicroRNAs: novel biomarkers for human cancer", Clin Chem 55, 623-631 (2009).
Bentwich, "Prediction and validation of microRNAs and their targets", FEBS Lett 579, 5904-5910 (2005).
Betancur, et al., "Dicer is dispensable for asymmetric RISC loading in mammals", RNA 18, 24-30 (2012).
Brennecke, et al., "bantam Encodes a Developmentally Regulated microRNA that Controls Cell Proliferation and Regulates the Proapoptotic Gene hid in *Drosophila*", Cell 113, 25-36 (2003).
Cao, et al., "A new plasmid-based microRNA inhibitor system that inhibits microRNA families in transgenic mice and cells: a potential new therapeutic reagent", Gene Therapy 23, 527-542 (2016).
Cao, et al., "Design and Function of a Plasmid-Based microRNA Inhibitor System In Vitro and In Vivo: Knockdown of the miR17-92 Cluster Reveals Multiple Defects", Endocrine Society's 94th Annual Meeting and Expo, Jun. 23-26, 2012, Houston TX.
Cao, et al., "MicroRNAs Play a Critical Role in Tooth Development", J Dent Res 89, 779-784 (2010).
Carthew, et al., "Origins and Mechanisms of miRNAs and siRNAs", Cell 136, 642-655 (2009).
Cheng, et al., "Antisense inhibition of human miRNAs and indications for an involvement of miRNA in cell growth and apoptosis", Nuc Acid Res 33, 1290-1297 (2005).
Cordes, et al., "miR-145 and miR-143 regulate smooth muscle cell fate and plasticity", Nature 460, 705-710 (2009).
Davis, et al., "Improved targeting of miRNA with antisense oligonucleotides", Nuc Acid Res 34, 2294-2304 (2006).
Davis, et al., "Potent inhibition of microRNA in vivo without degradation", Nuc Acid Res 37, 70-77 (2009).
De Pontual, et al., "Germline deletion of the miR-17-92 cluster causes growth and skeletal defects in humans", Nat Genet 43, 1026-1030 (2011).

(Continued)

*Primary Examiner* — Kimberly Chong
(74) *Attorney, Agent, or Firm* — Viksnins Harris Padys Malen LLP

(57) ABSTRACT

The present invention relates to plasmid-based miR inhibitory systems (PMIS), miR inhibitors and methods of use of these systems and inhibitors.

22 Claims, 20 Drawing Sheets

Specification includes a Sequence Listing.

(56) References Cited

OTHER PUBLICATIONS

Donze, et al., "RNA interference in mammalian cells using siRNAs synthesized with T7 RNA polymerase.", Nucleic Acids Res. 30(10), e46, 4 pages (2002).
Ebert, et al., "MicroRNA sponges: competitive inhibitors of small RNAs in mammalian cells", Nat Methods 4(9), 121-726 (2007).
Eckstein, "The versatility of oligonucleotides as potential therapeutics", Biol Ther 7, 1021-1034 (2007).
Elmen, et al., "LNA-mediated microRNA silencing in non-human primates", Nature 452, 896-899 (2008).
Friedman, et al., "Most mammalian mRNAs are conserved targets of microRNAs", Genome Res 19, 92-105 (2009).
Gantier, et al., "Analysis of microRNA turnover in mammalian cells following Dicer1 ablation", Nuc Acid Res 39, 5692-5703 (2011).
Gentner, et al., "Stable knockdown of microRNA in vivo by lentiviral vectors", Nat Methods 6, 63-66 (2009).
Gregory, et al., "The miR-200 family and miR-205 regulate epithelial to mesenchymal transition by targeting ZEB1 and SIP1", Nature Cell Biol 10, 593-601 (2008).
Hammond, "MicroRNA therapeutics: a new niche for antisense nucleic acids", TiMM 12, 99-101 (2006).
Haraguchi, et al., "A potent 2'-O-methylated RNA-based microRNA inhibitor with unique secondary structures", Nuc Acid Res 40, e58 (2012).
Haraguchi, et al., "Vectors expressing efficient RNA decoys achieve the long-term suppression of specific microRNA activity in mammalian cells", Nucleic Acids Res 37(6), e43 (2009).
He, et al., "MicroRNAs: small RNAs with a big role in gene regulation", Nat Rev Genet 5, 522-531 (2004).
Heo, et al., "TUT4 in concert with Lin28 suppresses microRNA biogenesis through pre-microRNA uridylation", Cell 138, 696-708 (2009).
Hutvagner, et al., "Sequence-specific inhibition of small RNA function", PLoS Biol 2, E98 (2004).
Krutzfeldt, et al., "Silencing of microRNAs in vivo with 'antagomirs'", Nature 438, 685-689 (2005).
Lee, et al. "The C. elegans heterochronic gene lin-4 encodes small RNAs with antisense complementarity to lin-14", Cell 75, 843-854 (1993).
Liu, et al., "MicroRNA regulatory networks in cardiovascular development", Dev Cell 18, 510-525 (2010).
Lu, et al , "A single anti-microRNA antisense oligodeoxyribonucleotide (AMO) targeting multiple microRNAs offers an improved approach for microRNA interference", Nuc Acid Res 37, e24 (2009).
Lu, et al., "An Analysis of Human MicroRNA and Disease Associations", PLoS One 3, e3420 (2008).
Lu, et al., "MicroRNA expression profiles classify human cancers", Nature 435, 834-838 (2005).
Meister, et al., "Sequence-specific inhibition of microRNA- and siRNA-induced RNA silencing", RNA 10, 544-550 :2004).
Orom, et al., "LNA-modified oligonucleotides mediate specific inhibition of microRNA function", Gene 372, 137-141 (2006).
Patent Cooperation Treaty, International Searching Authority, Search Report and Written Opinion for PCT/US2015/48986, 13 pages, dated Mar. 4, 2016.
Poy, et al., "A pancreatic islet-specific microRNA regulates insulin secretion", Nature 432, 226-230 (2004).
Sayed, et al., "MicroRNA-21 Targets Sprouty2 and Promotes Cellular Outgrowths", Mol Biol Cell 19, 3272-3282 (2008).
Scherr, et al., "Lentivirus-mediated antagomir expression for specific inhibition of miRNA function", Nuc Acid Res 35, e149 (2007).
Stenvang, et al., "MicroRNAs as targets for antisense-based therapeutics", Expert Opin Biol Ther 8, 59-81 (2008).
Szoka, et al., "Comparative Properties and Methods of Preparation of Lipid Vesicles (Liposomes),", Ann.Rev. Biophys. Bioeng. 9, 467-508 (1980).
Ventura, et al., "Targeted deletion reveals essential and overlapping functions of the miR-17 through 92 family of rniRNA clusters", Cell 132, 875-886 (2008).
Vermeulen, et al., "Double-stranded regions are essential design components of potent inhibitors of RISC function", RNA 13, 723-730 (2007).
Wang, et al., "MicroRNA-17-92, a Direct Ap-2α Transcriptional Target, Modulates T-Box Factor Activity in Orofacial Clefting", PLoS Genet 9, e1003785 (2013).
Xie, et al., "Long-term, efficient inhibition of microRNA function in mice using rAAV vectors", Nat Methods 9, 403-409 (2012).
Yu, et al., "microRNA 17/20 inhibits cellular invasion and tumor metastasis in breast cancer by heterotypic signaling", PNAS 107(18), 8231-8236 (2010).
Zhang, et al., "MicroRNAs Regulate Pituitary Development, and MicroRNA 26b Specifically Targets Lymphoid Enhancer Factor 1 (Lef-1), Which Modulates Pituitary Transcription Factor 1 (Pit-1) Expression", J Biol Chem 285, 34718-34728 (2010).

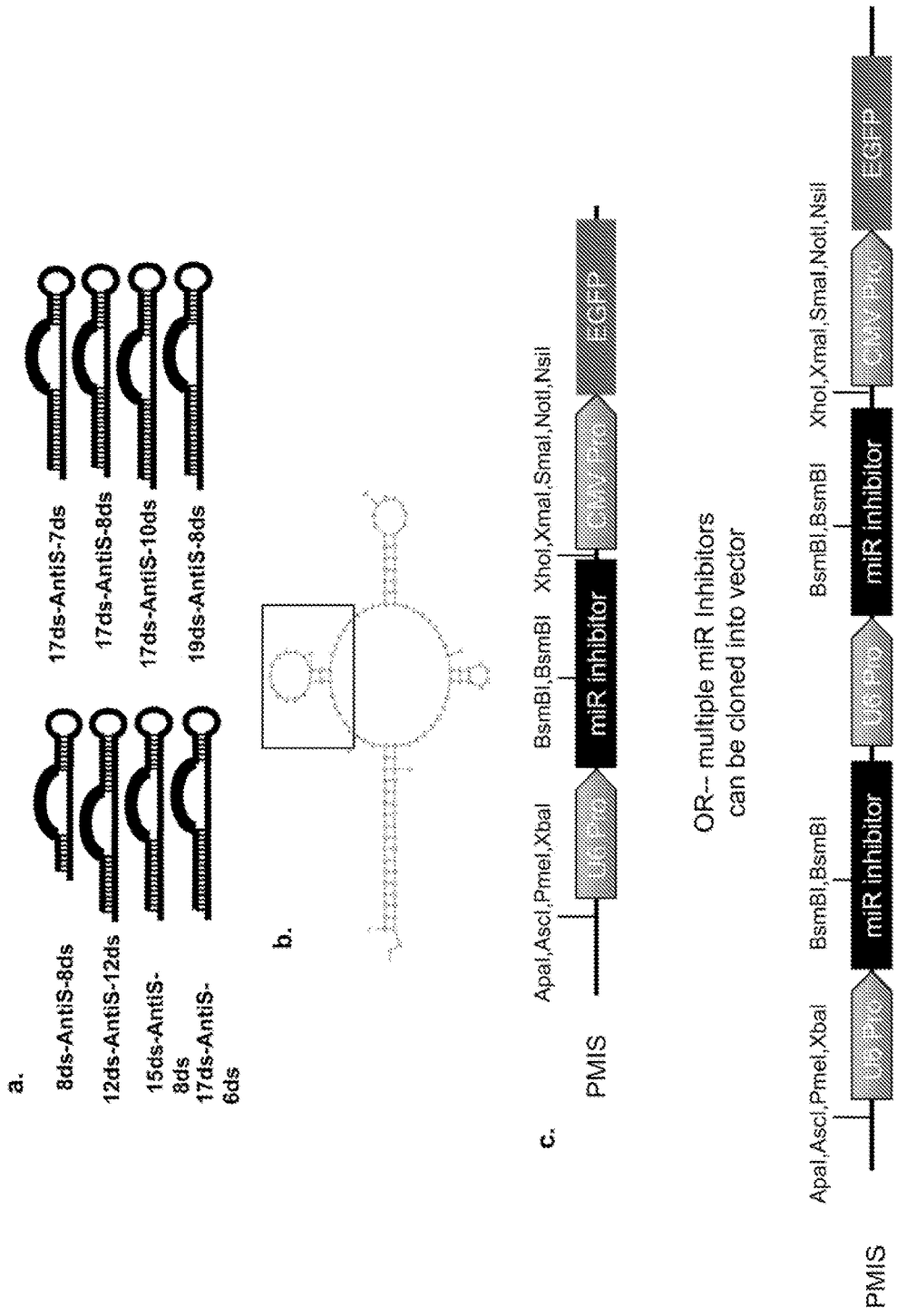

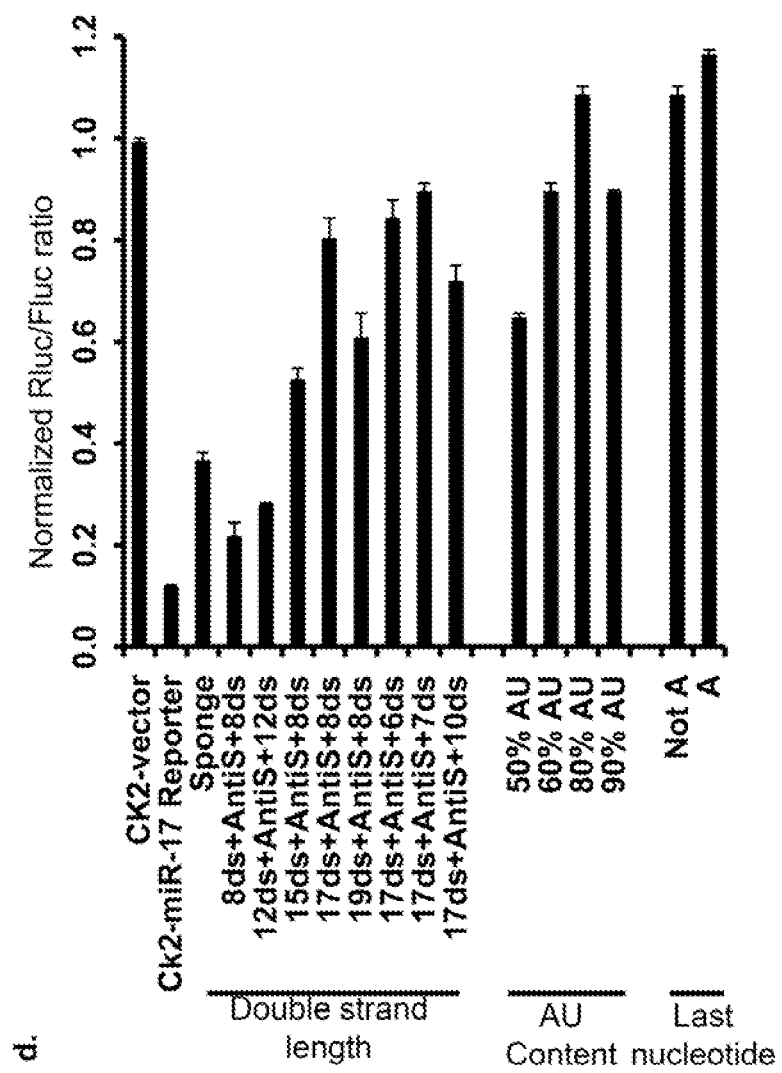

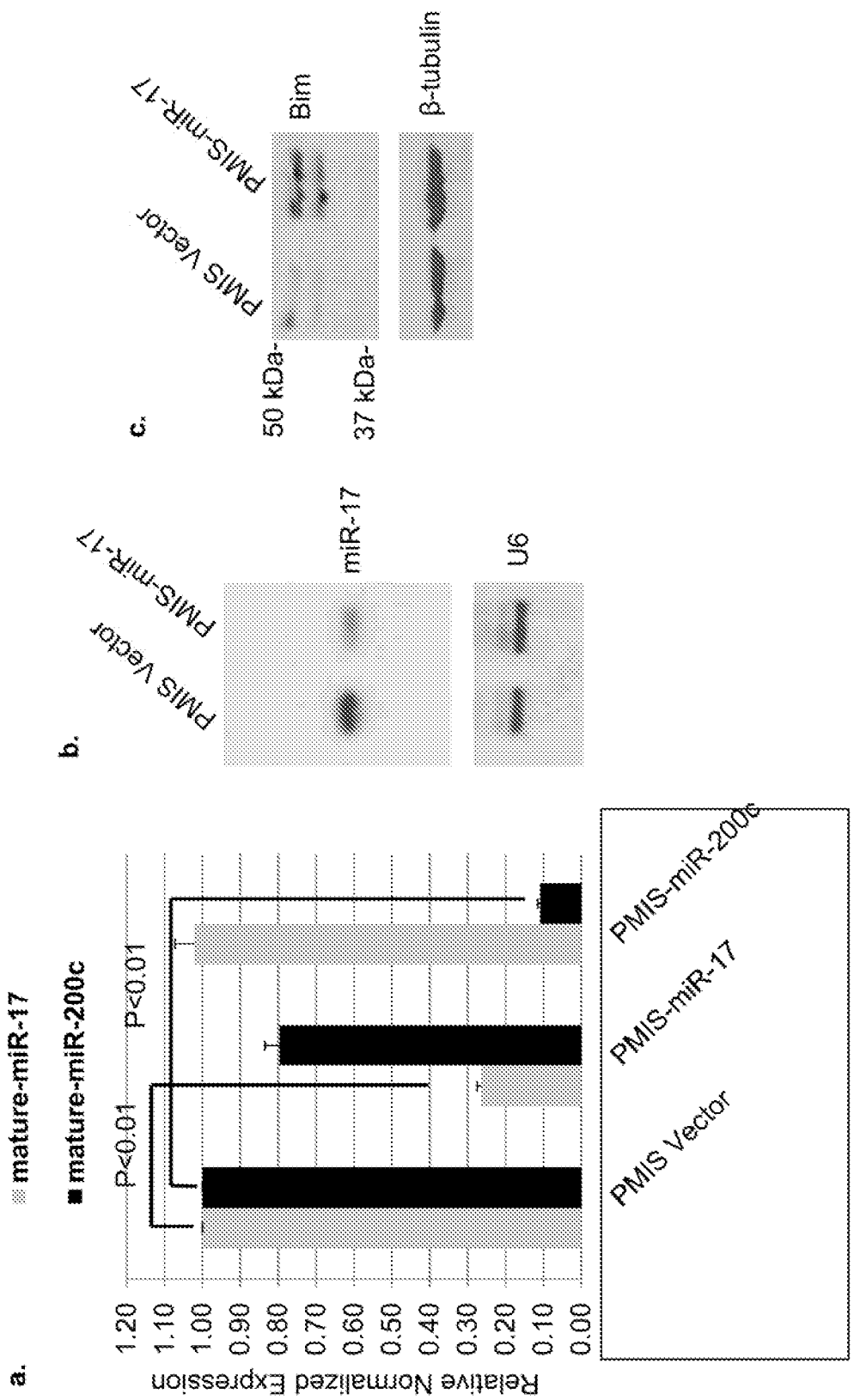
Fig. 2a,b,c

Fig. 3a a.

| Name | Sequence | SEQ ID NO |
|---|---|---|
| mmu-miR-17-5p | Caaagugcuuacagugcagguag | SEQ ID NO: 3 |
| PMIS-miR-17 | cuaccugcacuguaucaaagcacuuua | SEQ ID NO: 26 |
| PMIS-miR-17-mut-2 | cuaccugcacuguaucaaagcacuuAa | SEQ ID NO: 27 |
| PMIS-miR-17-mut-3 | cuaccugcacuguaucaaagcacuAua | SEQ ID NO: 28 |
| PMIS-miR-17-mut-4 | cuaccugcacuguaucaaagcacAuua | SEQ ID NO: 29 |
| PMIS-miR-17-mut-5 | cuaccugcacuguaucaaagcaGuuua | SEQ ID NO: 30 |
| PMIS-miR-17-mut-6 | cuaccugcacuguaucaaagcUcuuua | SEQ ID NO: 31 |
| PMIS-miR-17-mut-7 | cuaccugcacuguaucaaagGacuuua | SEQ ID NO: 32 |
| PMIS-miR-17-mut-8 | cuaccugcacuguaucaaaCcacuuua | SEQ ID NO: 33 |
| PMIS-miR-17-mut-9 | cuaccugcacuguaucaaUgcacuuua | SEQ ID NO: 34 |
| PMIS-miR-17-mut-10 | cuaccugcacuguaucaUagcacuuua | SEQ ID NO: 35 |
| PMIS-miR-17-mut-11 | cuaccugcacugAaucaaagcacuuua | SEQ ID NO: 36 |
| PMIS-miR-17-mut-12 | cuaccugcacuCuaucaaagcacuuua | SEQ ID NO: 37 |
| PMIS-miR-17-mut-13 | cuaccugcacAguaucaaagcacuuua | SEQ ID NO: 38 |
| PMIS-miR-17-mut-14 | cuaccugcaGuguaucaaagcacuuua | SEQ ID NO: 39 |
| PMIS-miR-17-mut-15 | cuaccugcUcuguaucaaagcacuuua | SEQ ID NO: 40 |
| PMIS-miR-17-mut-16 | cuaccugGacuguaucaaagcacuuua | SEQ ID NO: 41 |
| PMIS-miR-17-mut-17 | cuaccuCcacuguaucaaagcacuuua | SEQ ID NO: 42 |
| PMIS-miR-17-mut-18 | cuacAgcacuguaucaaagcacuuua | SEQ ID NO: 43 |
| PMIS-miR-17-mut-19 | cuacGugcacuguaucaaagcacuuua | SEQ ID NO: 44 |
| PMIS-miR-17-mut-20 | cuaGcugcacuguaucaaagcacuuua | SEQ ID NO: 45 |
| PMIS-miR-17-mut-21 | cuUccugcacuguaucaaagcacuuua | SEQ ID NO: 46 |
| PMIS-miR-17-mut-22 | cAaccugcacuguaucaaagcacuuua | SEQ ID NO: 47 |
| PMIS-miR-17-mut-23 | Guaccugcacuguaucaaagcacuuua | SEQ ID NO: 48 |
| PMIS-miR-17-mut-2+8 | cuaccugcacuguaucaaaCcacuuAa | SEQ ID NO: 49 |

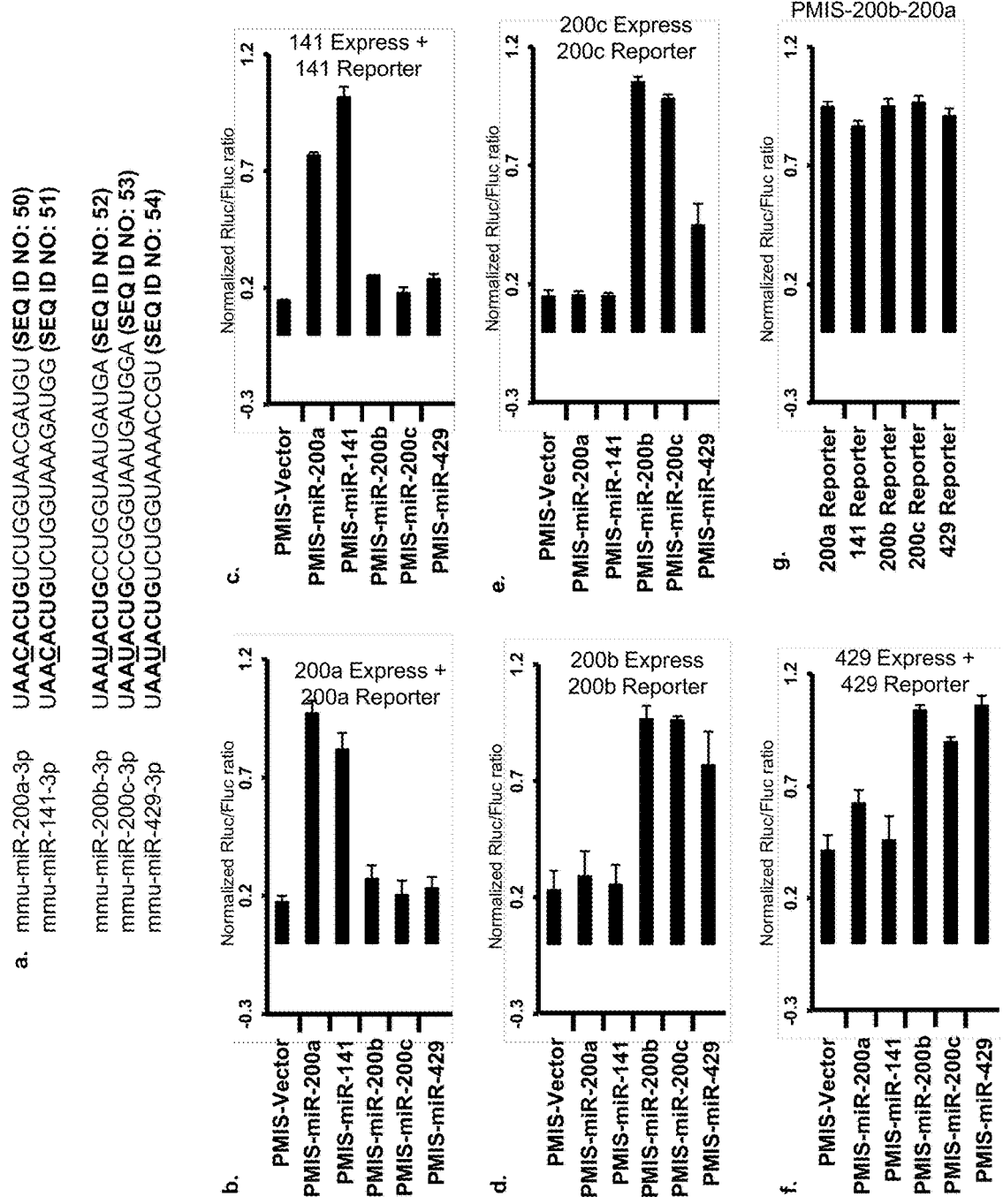

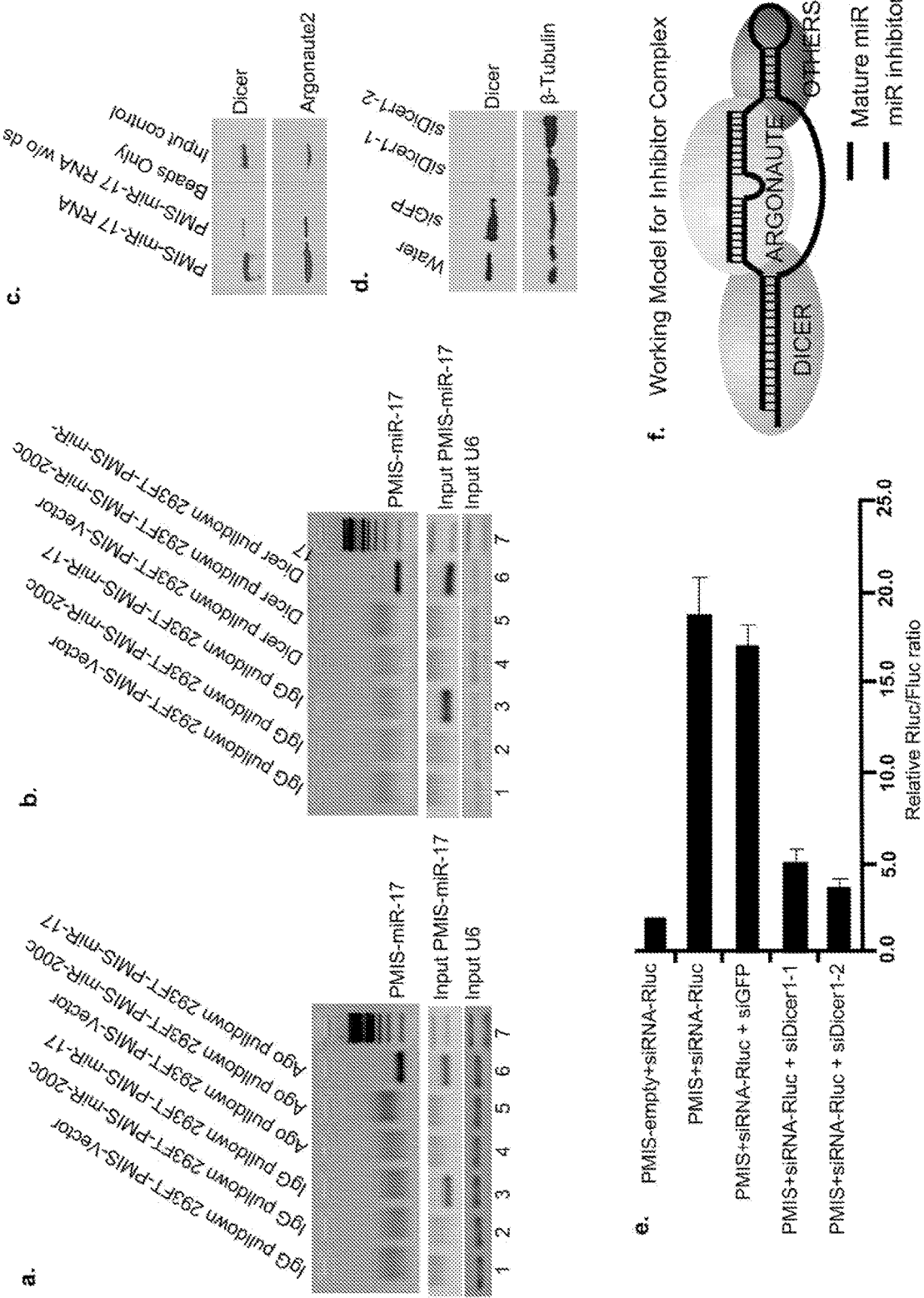

Fig. 6
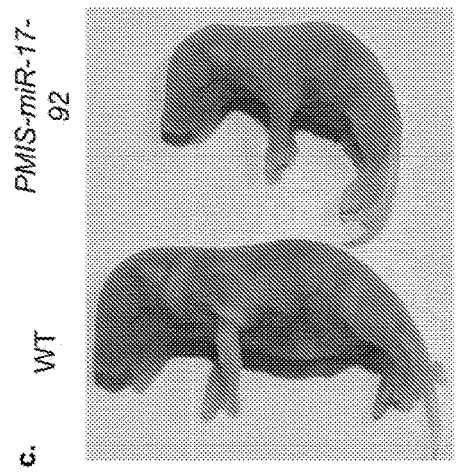
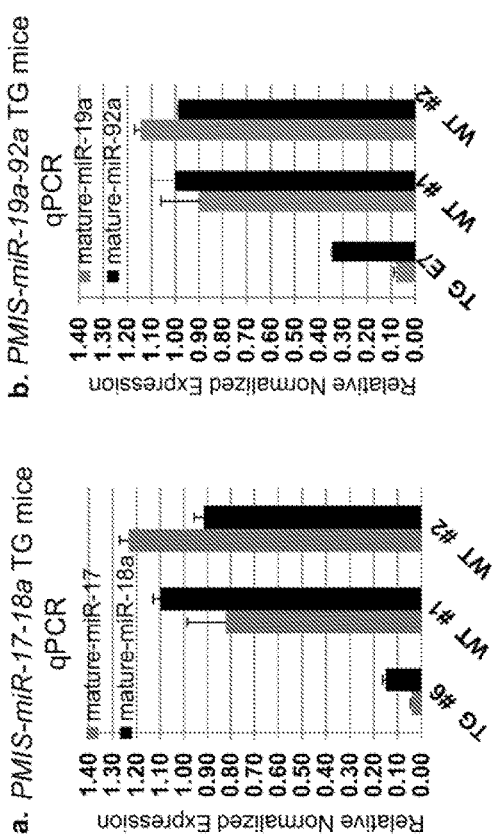
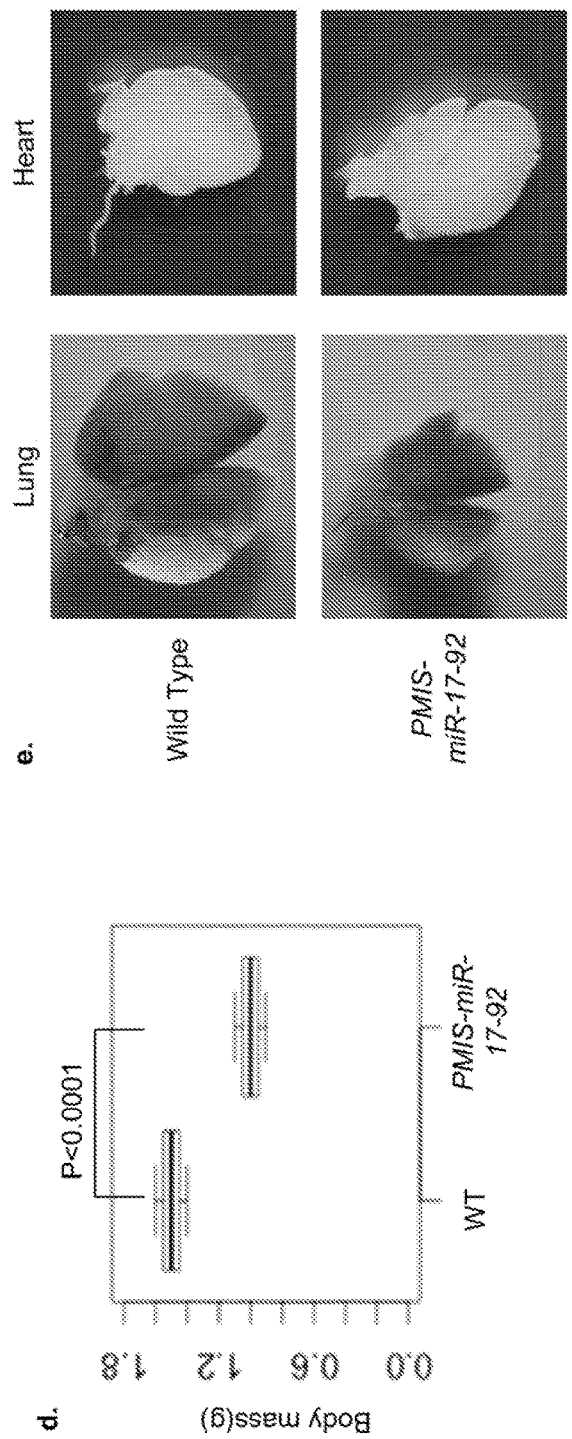

Breast Cancer
(Up-regulated (Targets)
    miRNA)
                        (Down-regulated  (Targets)
                Normal    miRNA)
                Mammary
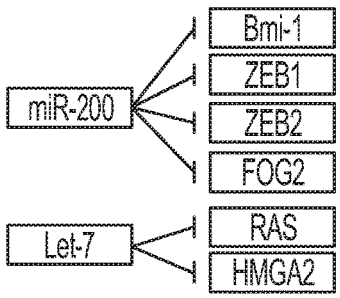
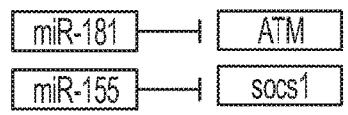
↓ Cancer Initiation
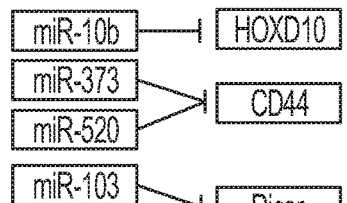
↓ Metastasis
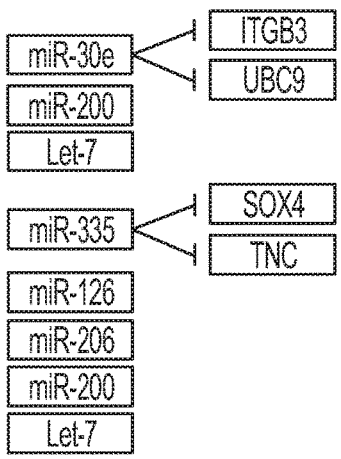
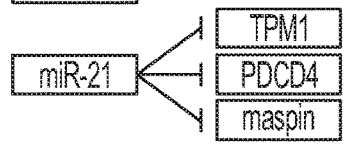
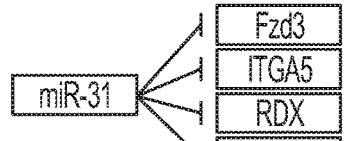
↓ Therapy Resistance
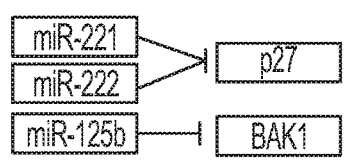
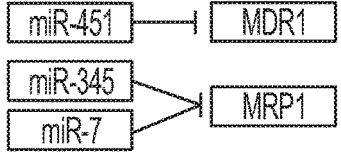
Fig. 13B

MICRORNA INHIBITOR SYSTEM AND METHODS OF USE THEREOF

RELATED APPLICATIONS

This application claims priority to United States Provisional Application No. 62/047,390 that was filed on Sep. 8, 2014.

SEQUENCE LISTING

The instant application contains a Sequence Listing which has been filed electronically in ASCII format and is hereby incorporated by reference in its entirety. Said ASCII copy, created on Feb. 12, 2019, is named 17023_148_US1_SL.txt and is 15,646 bytes in size.

STATEMENT REGARDING FEDERALLY SPONSORED RESEARCH

This invention was made with government support under DE13941 awarded by the National Institutes of Health. The government has certain rights in the invention.

BACKGROUND OF THE INVENTION

MicroRNAs or miRNAs are short sequences of RNA (20-24 nucleotide molecules) that function by altering the stability or translational efficiency of targeted mRNAs. There has been a significant amount of recent research into miRNAs that has attempted to determine their full scope, mechanism of action and disease association. Products associated with the understanding and clinical application of miRNAs will likely play a strong part in the future of medical care. Given the importance of miRs during different biological processes, tools for repression of miR function may be useful for research and have therapeutic potential. MicroRNAs are thought to regulate tumor progression and invasion via direct interaction with target genes within cells.

Current tools for the analyses of microRNA (miR) function rely on expensive and time consuming gene targeting mutagenesis or repetitive administration of chemically modified miR antagomirs. Accordingly, inexpensive, long-term, and safer (reduce side effects) system for treatment of various cancers, disease tissues, infections is needed.

SUMMARY OF THE INVENTION

In certain embodiments, the present invention provides a plasmid-based miR inhibitory system (PMIS) based on hairpin structures that uniquely characterize miR transcripts. The addition of short hairpin structure to antisense oligos greatly increased its inhibitory activity, by enhancing the binding of the antisense oligos to miRs. These structures may coordinate physical interactions with proteins that bring the antisense oligo close to the miR and dramatically facilitate their binding. The PMIS expresses anti miR antisense oligos flanked by hairpin structures and contain features including AU rich flanking sequences that are able to enhance miR efficiency of endogenous targets. In addition, the plasmid may be transiently or constitutively expressed depending on the vector or integration.

MicroRNA Inhibitor System

In certain embodiments, the present invention provides a microRNA inhibitor system comprising a nucleic acid vector and at least one expression cassette, wherein each expression cassette comprises a promoter operably linked to a miR inhibitor, wherein the miR inhibitor comprises an antisense oligonucleotide (ASO) having a 5' end and a 3' end, and wherein the mirR inhibitor is contiguously linked to a 5' flanking structure at the 5' end and a 3' flanking structure at the 3' end.

In certain embodiments, the vector is a plasmid. In certain embodiments, the vector is a viral vector. In certain embodiments, the vector is an Adenovirus, Adeno-associated virus, lentivirus, baculovirus, or any plasmid incorporated into any virus. In certain embodiments, the plasmids can be yeast, bacterial or mammalian replication competent and low or high copy number plasmids. In certain embodiments the miR Inhibitor is used without a vector as an in vitro transcribed RNA molecule introduced into cells using nano particles, protein systems or transfection reagents. In certain embodiments, the promoters can be Polymerase II or III driven promoters that express both eukaryotic and prokaryotic transcripts, can be either polyadenylated or non-polyadenylated, and any length. In certain embodiments, the plasmids may contain enhancer, silencer, splicing or other regulatory elements.

In certain embodiments, the 5' flanking structure is 5 to 20 nucleotides in length. In certain embodiments, the 5' flanking structure is 15 to 18 nucleotides in length. In certain embodiments, the 5' flanking structure is 17 nucleotides in length.

In certain embodiments, the 3' flanking structure forms a 3' duplex region of 5 to 20 basepairs in length. In certain embodiments, the 3' flanking structure forms a 3' duplex region of 5 to 8 basepairs in length. In certain embodiments, the 3' flanking structure forms a 3' duplex region 7 basepairs in length.

In certain embodiments, the 3' flanking structure is capable of forming a double stranded region with itself and a loop structure, and forms a double stranded region with the 5' flanking structure.

In certain embodiments, the each loop region is independently 6-18 nucleotides in length. In certain embodiments the 5' loop is 15-18 nucleotides in length. In certain embodiments, the middle loop is 8-11 nucleotides in length. In certain embodiments, the 3' loop is 6-12 nucleotides in length.

In certain embodiments, the 5' and/or 3' flanking structure independently encode about 50-90% A or U nucleotides. In certain embodiments, the 5' and/or 3' flanking structure independently encode about 60-90% A or U nucleotides. In certain embodiments, the 5' and/or 3' flanking structure independently encode about 75-85% A or U nucleotides.

In certain embodiments, the ASO is 18 to 26 nucleotides in length.

In certain embodiments, the promoter is a transiently expressed. In certain embodiments, the promoter is constitutively expressed. In certain embodiments, the promoter is a polII or polIII promoter. In certain embodiments, the polIII promoter is a U6 promoter. In certain embodiments, the polIII promoter is a mouse U6 promoter. In certain embodiments, the promoter is a poiII promoter. In certain embodiments, the promoter is a tissue-specific promoter. In certain embodiments, the promoter is an inducible promoter.

In certain embodiments, 3' flanking structure ends in an A nucleotide.

In certain embodiments, the nucleic acid is DNA.

In certain embodiments, the ASO is completely complimentary to a miR and binds with an affinity having a Kd equal or less than 100+/−5 nM.

In certain embodiments, the microRNA inhibitor system comprises multiple expression cassettes.

In certain embodiments, the microRNA inhibitor system further comprises a promoter operably linked to a reporter gene.

In certain embodiments, the seed sequence of the ASO is identical to the seed region of the target miR.

In certain embodiments, the 5' flanking structure is 17 nucleotides in length, wherein the 3' flanking structure forms a 3' duplex region 7 basepairs in length, wherein the 5' and 3' flanking structures independently include about 75-85% AU sequences, and wherein the 3' flanking structure ends in an A nucleotide.

MiR Inhibitor

In certain embodiments, the present invention provides a miR inhibitor of about 100 to 135 nucleotides in length, comprising an antisense oligonucleotide (ASO) having a 5' end and a 3' end, and wherein the mirR inhibitor is contiguously linked to a 5' flanking structure at the 5' end and a 3' flanking structure at the 3' end, wherein, the 3' flanking structure forms a double stranded region with itself and a loop structure, and forms a double stranded region with the 5' flanking structure.

In certain embodiments, the 5' and/or 3' hairpin structure independently encode about 50-90% A or U nucleotides. In certain embodiments, the 5' and/or 3' flanking structure independently encode about 60-90% A or U nucleotides. In certain embodiments, the 5' and/or 3' flanking structure independently encode about 75-85% A or U nucleotides.

In certain embodiments, the ASO is 18 to 26 nucleotides in length. In certain embodiments, 3' flanking structure ends in an A nucleotide.

In certain embodiments, the ASO is antisense to a miR and binds with a Kd equal or less than 100+/−5 nM.

In certain embodiments, the miR inhibitor further comprises a promoter operably linked to a reporter gene. In certain embodiments the miR Inhibitor is used without a vector as an in vitro transcribed RNA molecule introduced into cells using nano particles, protein systems or transfection reagents.

Methods of Inhibiting miR

In certain embodiments, the method of inhibiting miR comprising administering the system described above, wherein the system reduces the level of target miR by about 25% to 100%. In certain embodiments, the system reduces the level of target miR by about 90%.

In certain embodiments, the ASO irreversibly silences its target miRs. In certain embodiments, the target miR is miR-1, miR-7, miR-9, miR-10, miR-10a, miR-10b, miR-15, miR-15a, miR-15/16, miR-17, miR-17-92, miR-18a, miR-19a, miR-19a/b, miR-20a, miR-21, miR-23, miR-23a, miR-24, miR-25, miR-26, miR-26a, miR-27, miR-27a, miR-27b, miR-29, miR-30, miR-30e, miR-31, miR-32, miR-34, miR-34a, miR-34c, miR-44, miR-92, miR-92a, miR-96, miR-99a, miR-100, miR-101, miR-103, miR-106b, miR-107, miR-122, miR-122a, miR-122b, miR-124, miR-125, miR-125b, miR-126, miR-126b, miR-128, miR-129, miR-130, miR-133, miR-133a, miR-135, miR-137, miR-141, miR-143, miR-143/145, miR-145, miR-146a, miR-150, miR-152, miR-155, miR-181, miR-183, miR-192, miR-193b, miR-194, miR-195, miR-199a, miR-199b, miR-200, miR-200c, miR-203, miR-205, miR-206, miR-208a, miR-210, miR-214, miR-215, miR-218, miR-221, miR-222, miR-223, miR-224, miR-320, miR-326, miR-330, miR-331, miR-335, miR-342, miR-345, miR-363, miR-373, miR-375, miR-378, miR-423, miR-449a, miR-451, miR-483, miR-494, miR-495, miR-520, miR-520c, miR-590, miR-602, miR-615, miR-625, Let-7 and/or any microRNA endogenously expressed in or by mammalian species, yeast, bacteria or viruses (see FIGS. 12 and 13).

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides "Operably-linked" refers to the association two chemical moieties so that the function of one is affected by the other, e.g., an arrangement of elements wherein the components so described are configured so as to perform their usual function.

BRIEF DESCRIPTION OF DRAWINGS

FIG. 1. Optimization of miR inhibitor efficiency. a) miR inhibitor designs. Bold line indicates the specific inhibitor sequence that is complementary to the miR. Lighter line indicates the double stranded and stem loop RNA. b) Predication of RNA secondary structure of the final inhibitor design by RNA mfold (SEQ ID NO: 61). c) Structure of the vector construct used to transduce cells, either one or multiple miR inhibitors can be cloned into the vector. d) Effects of secondary structure length, local AU content and last A ribonucleotide on miR inhibitor efficiency. Normalized Rluc to Fluc ratio of miR reporter vector without miR-17 binding site was set as 100 percent. miR inhibitor designs were co-transfected with miR reporter containing a miR-17 binding site into HEK 293FT cells, which endogenously express miR-17. Rluc and Fluc activity was measured 48 hours after transfection. The sponge plasmid has six tandem miR-17 binding sites.

FIG. 2. Efficiency of the PMIS. a) PMIS-miR-inhibitors reduce specific miR expression. Real time PCR of mature endogenous miR-17 and miR-200c from 293 cells transfected with the indicated PMIS inhibitor. b) Northern blot of mature endogenous miR-17 from 293 cells transfected with PMIS-vector or PMIS-miR-17. U6 RNA is shown as a loading control. c) Western blot of Bim, a known target of miR-17 from cells transfected with the PMIS-vector or PMIS-miR-17. β-tubulin is shown as a loading control.

FIG. 4. Knockdown of the miR-200 family with a single plasmid. a) Sequence of mature miR 200 family members. The underlined nucleotide indicates the different ribonucleotide between two subfamilies in the seed region (bold). FIG. 4a discloses SEQ ID NOS 50-54, respectively, in order of appearance. b) Inhibition of miR-200a-3p with different PMIS-miR inhibitors. PMIS empty vector or various PMIS-miR inhibitors were co-transfected with miR-200a expression plasmid and miR reporter vector containing a miR-200a binding site into HEK 293FT cell. Rluc and Fluc activity was measured 48 hours after transfection. c) Inhibition of miR-141-3p with different PMIS-miR inhibitors. d) Inhibition of miR-200b-3p with different PMIS-miR inhibitors. e) Inhibition of miR-200c-3p with different PMIS-miR inhibitors. f) Inhibition of miR-429-3p with different PMIS-miR inhibitors. g) A single plasmid expressing both PMIS-miR-200a-200b inhibits all five members of the miR-200 family.

FIG. 5. miR inhibitor interaction with RISC. a) Pull-down of miR inhibitor using Argonaute 2 antibody. PCR primers were used to detect PMIS-miR-17 after pull-down, U6 used as loading control. IgG antisera was used as a control and PMIS-miR-200c transfected as a PCR control. b) Pull-down of miR inhibitor using a Dicer antibody. Controls were as in panel A. c) Pull-down of Argonaute 2 and Dicer with biotinylated PMIS-miR-17. Biotinylated PMIS-miR-17 RNA or PMIS-miR-17 RNA without the double stranded regions were incubated with 293 cell extracts, washed, denatured and analyzed by PAGE. Western blot was performed using Dicer and Argonaute antibodies. Proteins were detected using ECL reagents (GE HealthCare). d) Western blot of Dicer after knockdown of Dicer with siRNA. Cell lysates (15 µg) were resolved by PAGE after transfection with siGFP, siDicer 1-1 and siDicer 1-2 (two different siRNA constructs) or water as a control. Western blot was performed using Dicer antibody and β-tubulin antibody as a loading control. e) Knockdown of Dicer impaired miR inhibitor function. Rluc vector and in-vitro transcribed siRNA targeting Rluc was co-transfected with miR inhibitor to siRNA-Rluc and in-vitro transcribed siRNA targeting GFP or two different sites of the Dicer transcript. Rluc and Fluc activity was measured 48 hours after transfection. f) A working model for the PMIS association with proteins in the RISC: middle ellipsoid is Argonaute protein, left ellipsoid is Dicer protein, and right ellipsoid is other protein(s). Short line at center of Argonaute protein is mature miR, long line in contact with Dicer, Argonaute and other protein(s) is PMIS-miR inhibitor.

FIG. 6. PMIS-miR-17-92 function in mice. a) Realtime PCR of endogenous mature miR-17 and miR-18a in PMIS-miR-17-18a transgenic mice and control littermates. Taqman probes were used to analyze miR expression from mouse tails. b) Realtime PCR of endogenous mature miR-19a and miR-92a in PMIS-miR-19a-92a transgenic mice and control littermates. Taqman probes were used to analyze miR expression from mouse tails. c) PMIS-miR-17-18a and PMIS-miR-19a-92a mice were mated to produce the PMIS-miR-17-92 embryos which are perinatal lethal. The E18.5 PMIS-miR-17-92 embryos are smaller than WT embryos. d) The weight of the PMIS-miR-17-92 embryos are less than their littermates. e) The PMIS-miR-17-92 embryos have small lungs and normal heart development.

FIG. 10 discloses SEQ ID NOS 55, 10, 56-57, 2, 18, 58-59, 6, 9, 9, 17, 17, 12 and 60, respectively, in order of appearance.

Shown are pathological processes in the cardiovascular system and the miRNAs that control these processes. miRNAs regulate cardiomyocyte proliferation, hypertrophy, and apoptosis. Other miRNAs act on fibroblasts and inflammatory cells to control fibrosis and inflammation, respectively. Blood vessel growth and stability, and angiogenesis and smooth-muscle cell proliferation, are also regulated by miRNAs acting on endothelial cells and smooth-muscle cells, respectively. Credit: H. McDonald/Science Translational Medicine".

Figure 13A:
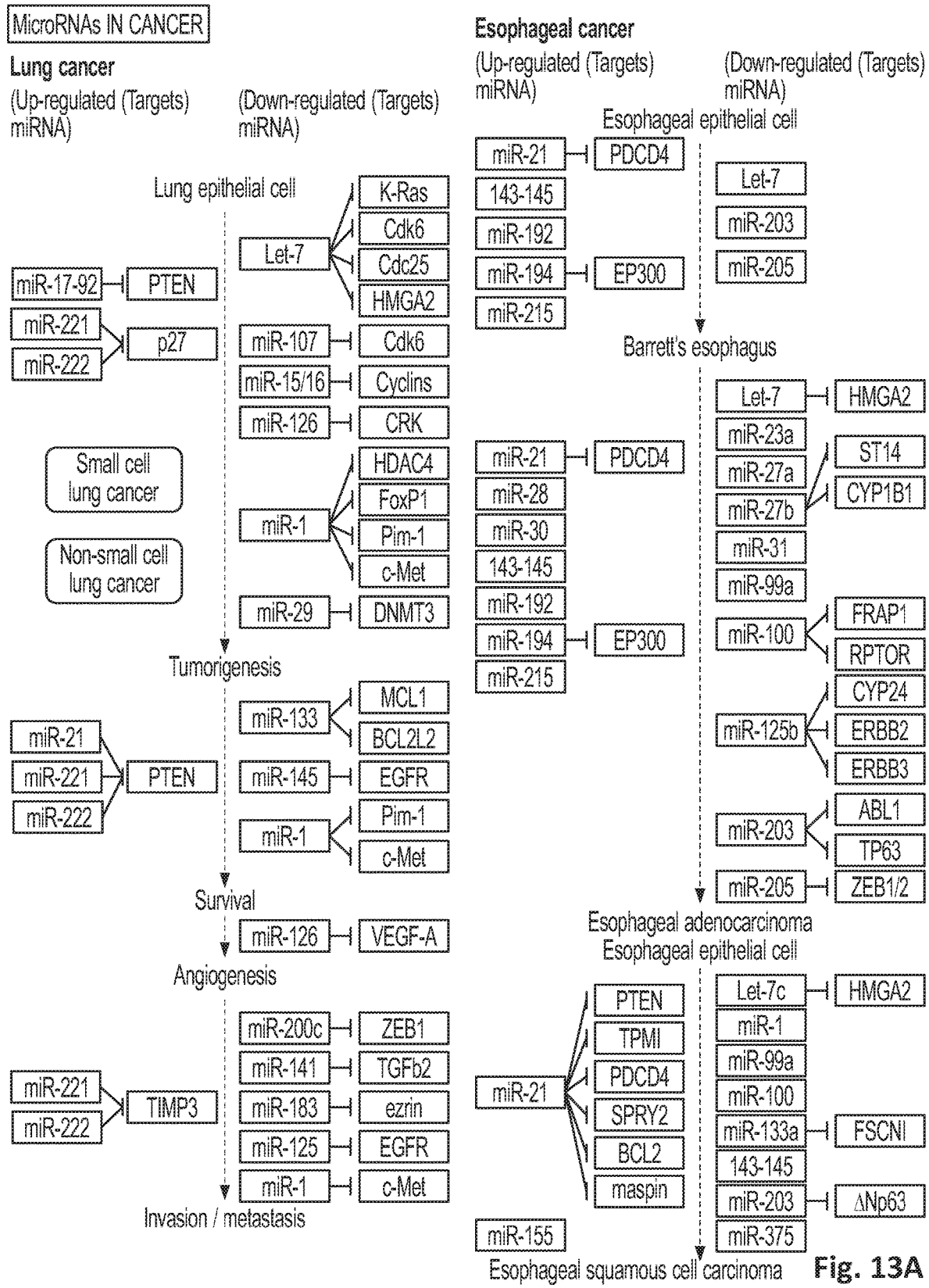
Figure 13A:
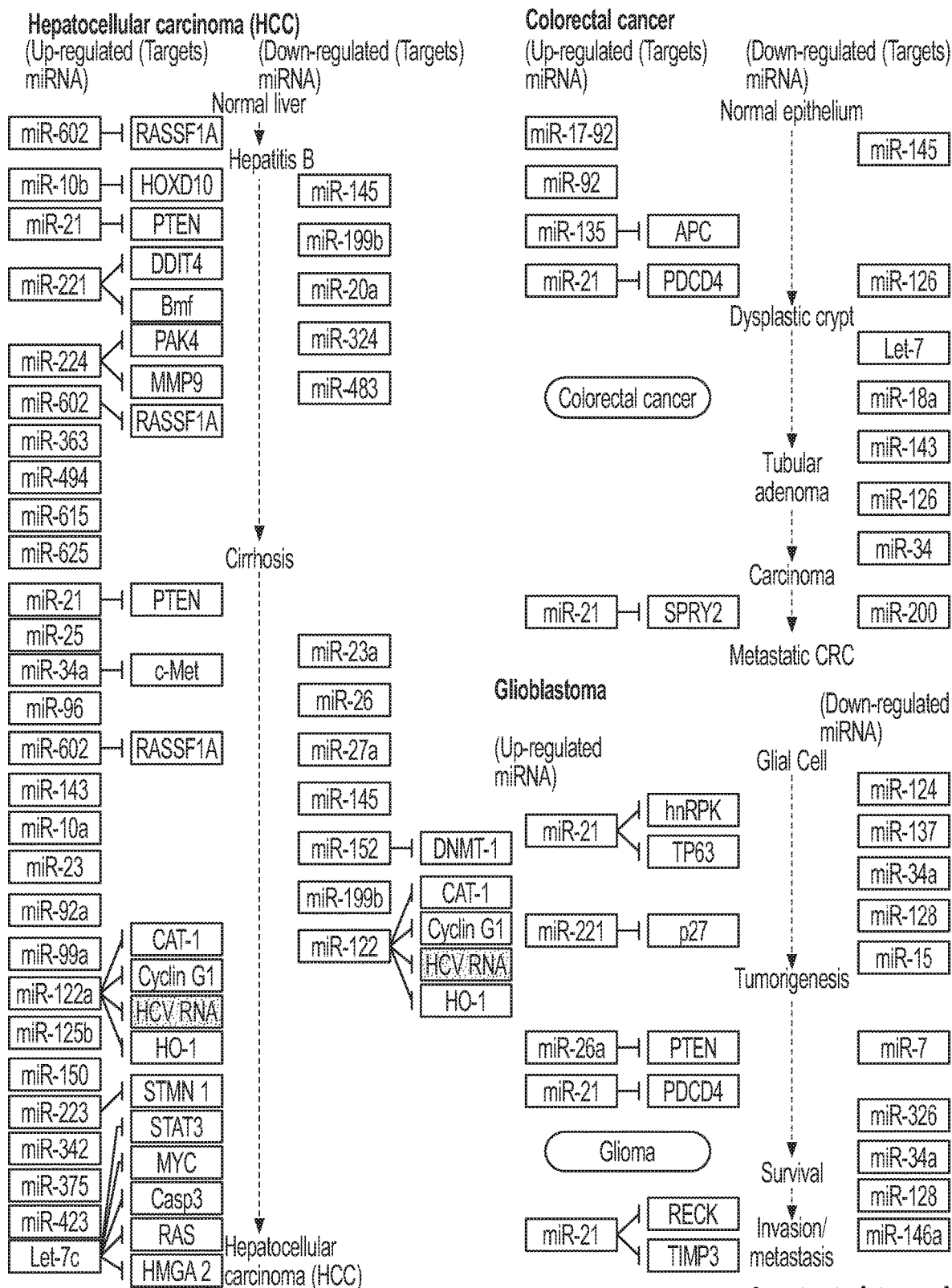
Figure 13B:
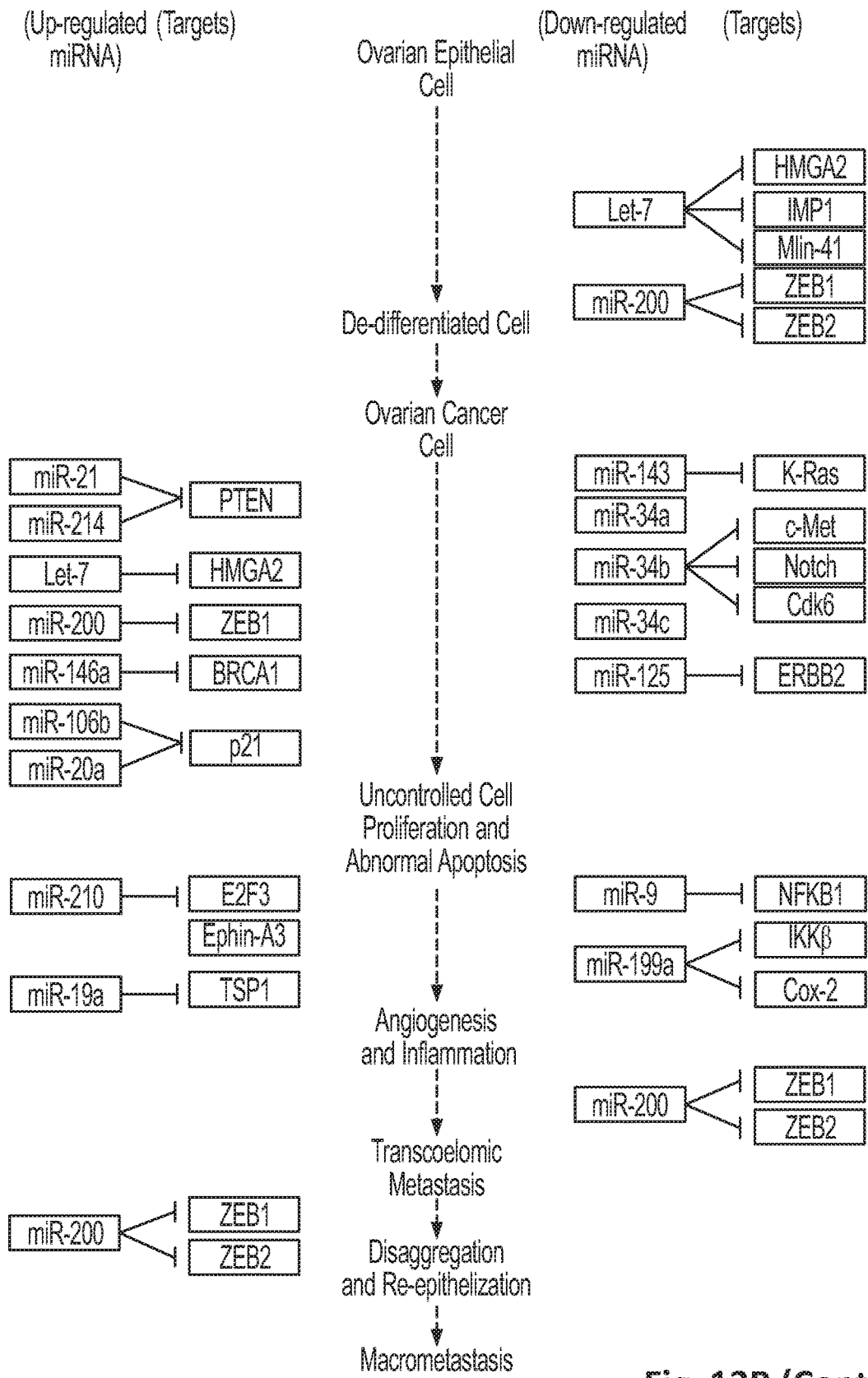
Figure 13B:
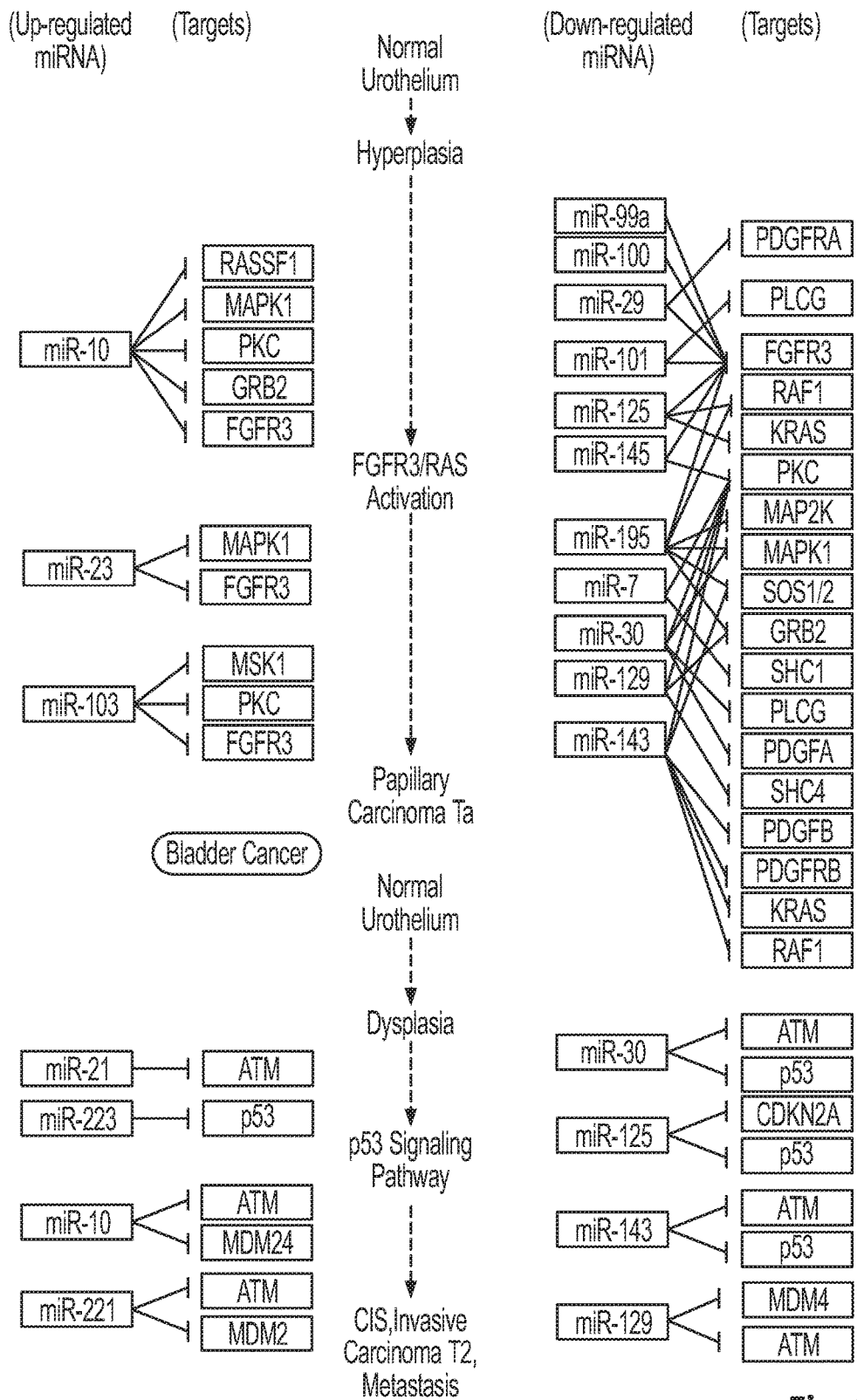
Figure 13B:
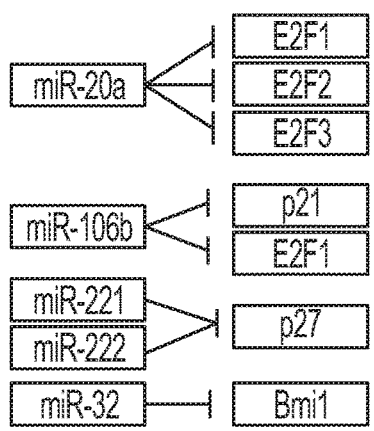

FIGS. 13A and 13B show miRs that are associated with cancer.

DETAILED DESCRIPTION OF THE INVENTION

Currently, one way to attenuate miR activity is administration of antisense oligos into cells that compete for binding with endogenous targets. A limitation of the currently used miR inhibitors resides in their inability to be retained in the tissues after cell division and they must be reapplied to maintain their effectiveness. To address these limitations and promote long-term repression of specific miRs, several plasmid and/or viral vectors expressing antagomirs, sponges, eraser and Tough Decoy (TuD) RNA molecules have been reported (Scherr, M. et al. Lentivirus-mediated antagomir expression for specific inhibition of miRNA function. *Nuc. Acid Res.* 35, e149 (2007); Sayed, D. et al. MicroRNA-21 targets Sprouty2 and promotes cellular outgrowths. *Mol. Biol. Cell* 19, 3272-3282 (2008); Ebert, M. S., Neilson, J. R. & Sharp, P. A. MicroRNA sponges: competitive inhibitors of small RNAs in mammalian cells. *Nature Methods* 4, 721-726 (2007); Haraguchi, T., Ozaki, Y. & Iba, H. Vectors expressing efficient RNA decoys achieve the long-term suppression of specific microRNA activity in mammalian cells. *Nuc. Acid Res.* 37, e43 (2009)).

In certain embodiments, the present invention provides a plasmid-based miR inhibitor system (PMIS) based on hairpin structures that uniquely characterize miR transcripts, that inhibits miR activity in cells and mice. The PMIS engineered optimal secondary structure and flanking sequences form a stable complex with the miR, Argonaute and Dicer proteins. The addition of short hairpin structure to antisense oligos greatly increased its inhibitory activity, by enhancing the binding of the antisense oligos to miRs. The miR Inhibitor can be used as an in vitro transcribed RNA molecule without the need for a vector to express it in cells. The RNA miR inhibitor molecule can be introduced into any cell, tissue or living organism without a vector to inhibit microRNAs.

In cells, one PMIS can effectively inhibit miR family members that share the same seed sequence. The PMIS system can dissect different functions of miRs within miR cluster.

This is a new tool to study the role of miR regulation during development in animals, in cells and tissues, and as a therapeutic reagent in cancer and other diseases with little or no toxicity, induced long-term repression of miRNA, and has a low cost.

Promoters

The present invention further provides an expression cassette containing a promoter contiguously linked to a nucleic acid described herein. In certain embodiments, the promoter is a polII or a polIII promoter, such as a U6 promoter (e.g., a mouse U6 promoter). In certain embodiments, the expression cassette further contains a marker gene. In certain embodiments, the promoter is a polII promoter. In certain embodiments, the promoter is a tissue-specific promoter. In certain embodiments, the promoter is an inducible promoter. In certain embodiments, the promoter is a polIII promoter. In certain embodiments, the promoter is an inducible promoter. In certain embodiments, the expression cassette uses a constitutive promoter, tissue-specific promotes, development-specific promotes, regulatable promoter or viral promoter.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter.

Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

Expression Cassettes

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Antisense inhibition" refers to the production of antisense RNA transcripts capable of suppressing the expression of protein from an endogenous gene or a transgene.

Vectors

In certain embodiments, the vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation. In certain embodiments the vector is pSilencer 4.1 (Ambion). In certain embodiments the vector is pPMIS-TGA vector (Transgene A Vector). In certain embodiments the vector has #40 antirepressor, U6 promoter, and SAR+ poly A sequence. In certain embodiments the vector is pPMIS-TGB vector (Transgene B Vector). In certain embodiments the vector has same features as pPMIS-TGA vector but contains different cloning sites. In certain embodiments the vector is Amp resistant, puromycin and/or neomycin resistant.

In certain embodiments, the vector is an adenoviral, lentiviral, adeno-associated viral (AAV), poliovirus, HSV, or murine Maloney-based viral vector. In certain embodiments the vector is pLL3.7 vector. In certain embodiments the vector is any Polymerase II or III expression vector and/or transgenic vector.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi-synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed. The described miR Inhibitor can also be introduced into host cells as an in vitro transcribed RNA molecule, without the use of a vector. This miR Inhibitor RNA molecule works exactly like the Plasmid-Based miR Inhibitor to inhibit microRNA function.

Physical methods to introduce a preselected DNA into a host cell include calcium phosphate precipitation, lipofection, particle bombardment, microinjection, electroporation, nanoparticles and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human, cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR and/or Northern blotting may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into a miR inhibitor.

Methods for Introducing the Expression Cassettes of the Invention into Cells

The inhibitory nucleic acid material (e.g., an expression cassette encoding a miR inhibitor) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, nanoparticles, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the miR inhibitor together with a promoter to control transcription. The promoter characteristically has a specific nucleotide sequence necessary to initiate transcription. The exogenous nucleic acid material may further include additional sequences (i.e., enhancers) required to obtain the desired transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of miR inhibitor generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a miR inhibitor sequence that are in the cell.

In addition to at least one promoter and at least one heterologous nucleic acid sequence encoding the miR inhibitor, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the miR inhibitor (s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the nucleic acid sequence of interest.

The instant invention also provides methods for genetically modifying cells of a mammalian recipient in vivo. According to one embodiment, the method comprises introducing an expression vector for expressing a miR inhibitor sequence in cells of the mammalian recipient in situ by, for example, injecting the vector into the recipient.

Delivery Systems for Delivering MicroRNAs and PMIS MicroRNA Inhibitors to Human and Murine Cells and Tissues A wide range of nano-sized complexes, nanoparticles, microparticles and lipid based delivery systems are used to deliver microRNAs and PMIS microRNA Inhibitors to human and murine cells and tissues. These include synthetic cationic polymers such as polyethylenimine and natural polymers such as chitosan that can form complexes with the PMIS and microRNAs. The PMIS and microRNAs can be loaded into cationic, anionic and neutral liposomes. Also, the PMIS and microRNAs can be loaded into biodegradable synthetic polymers such as polylactide-co-glycolide (PLGA), PLA, polycaprolactone (PCL), polyanhydrides (PA). This list of provided materials is not exhaustive and we often use combinations and permutations of these materials such as preparing PLGA and PEI. A wide range of cell binding or cell targeting ligands can be conjugated to these delivery systems including (but not limited to) transferrin, cell penetrating peptides like RGD or TAT, aptamers, galactose and mannose.

A polymeric microparticle core as described herein can comprise one or more polymers. Polymers can be selected from the group consisting of biocompatible and/or biodegradable polymers. As used herein, the term "biodegradable" refers to the ability of a composition to erode or degrade in vivo to form smaller chemical fragments. Degradation may occur, for example, by enzymatic, chemical or physical processes. Non-limiting examples of biodegradable polymers that can be used in aspects of the invention include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer) and PLGA. PEG/PBT polymers are commercially available from OctoPlus Inc, under the trade designation PolyActive™. Non-limiting examples of biodegradable copolymers or multiblock copolymers include the ones described in U.S. Pat. Nos: 5,980,948 and 5,252,701, the contents of which are incorporated herein by reference in their entirety.

Other biodegradable polymer materials include biodegradable terephthalate copolymers that include a phosphorus-containing linkage. Polymers having phosphoester linkages, called poly(phosphates), poly(phosphonates) and poly(phosphites), are known in the art. See, for example, Penczek et al., Handbook of Polymer Synthesis, Chapter 17: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference in their entirety.

Biodegradable polyhydric alcohol esters can also be used for the purposes of the invention (See U.S. Pat. No. 6,592,895, which is incorporated herein by reference in its entirety). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon a-amino acids (such as elastomeric copolyester amides or copolyester urethanes, as described in U.S. Pat. No. 6,503,538, which is incorporated herein by reference in its entirety).

In one embodiment, the polymeric microparticle core described herein comprises poly(lactide-co-glycolide) (PLGA). In certain embodiments, the polymeric microparticle core described herein comprises at least about 20%, at least about 30%, at least about 40%, at least about 50%, at least about 60%, at least about 70%, at least about 80%, at least about 90%, at least about 95%, about 98%, about 99% or 100% of PLGA.

In general, any biocompatible material well known in the art for fabrication of microparticles can be used in embodiments of the microparticle described herein. Accordingly, a microparticle comprising a lipidic microparticle core is also within the scope of the invention. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) Ann. Rev. Biophys. Bioeng. 9: 467, Deamer and Uster (1983) Pp. 27-51 In: Liposomes, ed. M. J. Ostro, Marcel Dekker, New York, and the like.

The cationic dendrimer as described herein is generally a repeatedly branched and roughly spherical molecule with one or more positively-charged functional groups. In one embodiment, the cationic dendrimer is symmetric around the core, and generally adopts a roughly spherical three-dimensional morphology. In a particular embodiment, the cationic dendrimer used for surface modification of the microparticle core is poly(amidoamine) or PAMAM. The core of PAMAM is a diamine (commonly ethylenediamine), which is reacted with methyl acrylate, and then another ethylenediamine to make the generation-0 (G-0) PAMAM. Successive reactions create higher generations, which tend to have different properties. Lower generations can be considered as flexible molecules with no appreciable inner regions, while medium sized (G-3 or G-4) can have internal space that is essentially separated from the outer shell of the dendrimer. Very large (G-7 and greater) dendrimers can be considered as roughly solid particles with very dense surfaces due to the structure of their outer shell. In one embodiment, the outer surface of the microparticle core is modified with PAMAM Generation-3.

Without limitations, in some embodiments, other positively-charged polymer molecules can also be used to modify the outer surface of the microparticle core described herein. Examples of positively-charged polymers include, but are not limited to, polyamino acids such as polylysine, polyhistidine, polyornithine, polycitrulline, polyhydroxylysine, polyarginine, polyhomoarginine, polyaminotyrosine, and protamines. Other suitable positively-charged polymers include, but are not limited to, polydiaminobutyric acid, polyethyleneimine, polypropyleneimine, polyamino(meth)acrylate, polyaminostyrene, polyaminoethylene, poly(aminoethyl)ethylene, polyaminoethylstyrene, diethyl amino ethyl cellulose, poly-imino tyrosine, cholestyramine-resin, poly-imino acid, 1,5-dimethyl-1,5-diazaundecamethylene polymethobromide (hexadimethrine bromide), chitosan, poly(amidoamine) dendrimers, and combinations thereof.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic miR inhibitor" refers to any siRNA that has a beneficial effect on the recipient. Thus, "therapeutic miR inhibitor" embraces both therapeutic and prophylactic miR inhibitor.

Administration of miR inhibitor may be accomplished through the administration of the nucleic acid molecule encoding the siRNA. Pharmaceutical formulations, dosages and routes of administration for nucleic acids are generally known.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Example.

In vivo mammalian introduction of the miR Inhibitor DNA into the genome of a species can be accomplished using gene targeting systems. The miR Inhibitor can be inserted into the genome of any animal using the ROSA 26 loci for either continuous or induced expression of the miR Inhibitor. In additional a transgenic animal can be produced expressing the miR Inhbitor by pronuclear injection and insertion into nonspecific chromatin. Additional gene can be linked to the expression of the miR Inhibitor in animals.

Example 1

MicroRNAs (miRs) are short non-coding RNA molecules, about 22 nucleotides long, that regulate messenger RNA (mRNA) transcripts post-transcriptionally through binding to complementary sequences on target mRNA[1-4]. The human genome may contain over 1500 miR species (miRBase, release 18) and it has been estimated that more than half of protein coding genes could be regulated by miRs[5, 6]. Since the first discovery in 1993, miRs have been shown to be involved in the regulation of a broad range of biological processes and the malfunction of miRs are associated with many human diseases[7-16].

Given the importance of miRs during different biological processes, tools for repression of miR function will not only be useful for research but also have therapeutic potential. Currently, one method to attenuate miR activity is administration of antisense oligos into cells that compete for binding with endogenous targets. These include anti-miR antisense oligonucleotides (AMO), which has some or all of the ribonucleotides modified, such as 2'-O-methylated RNA[17-19], locked nucleic acids (LNA) or 2' methoxyethylated RNA[20, 21]. Other modifications of these AMOs include phosphorothioate substitutions, addition of flanking sequences and lipids[22, 23]. These modifications can increase their affinity towards miR sequences and protect the oligos from processing by cellular nucleases. A limitation of these miR inhibitors resides in their inability to be retained in the tissues after cell division and they must be reapplied to maintain their effectiveness. To address these limitations and promote long-term repression of specific miRs, several plasmid and/or viral vectors expressing antagomirs, sponges, eraser and Tough Decoy (TuD) RNA molecules have been reported[24-27]. Other chemically modified antisense oligonucleotides (ASOs) with a 2'-fluoro/2' methoxyethyl modified ASO motif improved in vivo inhibition of miR activity[28]. This system and others can inhibit miR activity without degradation of the miR[28, 29].

We report a new plasmid-based miR inhibitory system (PMIS) based on hairpin structures that uniquely characterize miR transcripts. The addition of short hairpin structure to antisense oligos greatly increased its inhibitory activity. These structures may coordinate physical interactions with proteins that bring the antisense oligo close to the miR and dramatically facilitate miR binding. The PMIS expresses anti-miR antisense oligos flanked by hairpin structures and contain features including AU rich flanking sequences and the plasmid may be transiently or constitutively expressed depending on the vector or integration. The PMIS effectively knocks down specific miRs in cells based on the anti-miR antisense sequence. More impressively, the PMIS inhibits miR expression in mice and can be used to dissect the function of miRs within clusters. The PMIS effectively inhibits miR expression in cells and tissues and is a potential therapeutic reagent for cancer and diseases with no toxicity and low cost.

Results

Design and Optimization of the PMIS

The PMIS design started with an anti-miR oligodeoxyribonucleotide based approach that expressed a nucleic acid sequence that is antisense to the miR[22, 30-34]. The antagomirs used in our study bind to the complete miR sequence including the seed region and flanking sequences to enhance the specificity and binding affinity of the antagomirs. The antagomir sequence was ligated to a custom designed ~120 nt RNA secondary structure that facilitates its function, stability and processing. The initial design began with an 8 nt double stranded (ds) sequence flanking each end of the antagomir (bold line), 8ds-AntiS-8ds (FIG. 1a). Multiple constructs were designed with different lengths of each ds region and eight of these are shown and the complete construct with a box highlighting the antagomir is shown (FIG. 1a, b). The PMIS-miR-inhibitors have a U6 promoter followed by a miR inhibitor, and if required a second U6 promoter followed by different miR inhibitor for cell transductions and transfections (FIG. 1c).

Several RNA elements, including double stranded regions, local AU content and the last nucleotide of the miR binding site influence miR recognition of its endogenous targets[35]. We reasoned that including these elements might enhance miR binding to the inhibitor (antagomir) that has a single miR binding site. A series of miR-17 antisense sequences (inhibitor) were constructed containing different flanking regions. To test the efficiency of these different designs, the inhibitors were co-transfected with a miR-17 reporter that has the miR-17 binding site cloned after the luciferase gene into HEK 293FT cells. miR-17 was used to test the inhibitor design, as miR-17 is one of highest expressed miRs. A miR sponge plasmid that has 6 tandem miR-17 binding sites was used as a control. These data demonstrate that the optimal miR inhibitor has a 17 nt double stranded RNA region at the 5' end and 7 nt double stranded sequence at the 3' end (17ds+AntiS+7ds), local AU content is 80%, and the last nucleotide is an A (FIG. 1d). This miR inhibitor recovers over 90% of the inhibition of luciferase activity by endogenous miR-17 (FIG. 1d).

The miR-17 inhibitor (PMIS-miR-17) reduced endogenous mature miR-17 levels to approximately 25% in 293 cells, while the miR-200c inhibitor (PMIS-miR-200c) does not change the level of miR-17 (FIG. 2a). PMIS-miR-200c inhibits miR-200c approximately 90% but does not affect miR-17 levels (FIG. 2a). A Northern blot of miR-17 expression after transduction of the PMIS-miR-17 inhibitor in 293 cells demonstrated reduced miR-17 compared to PMIS vector alone (FIG. 2b). Bim expression, a proapoptotic gene involved in B-cell development and a known target of miR-17[36], was elevated in cells transfected with PMIS-miR-17 compared to cells with empty vector (FIG. 2c).

Specificity of the miR Inhibitor

Figure 3B:
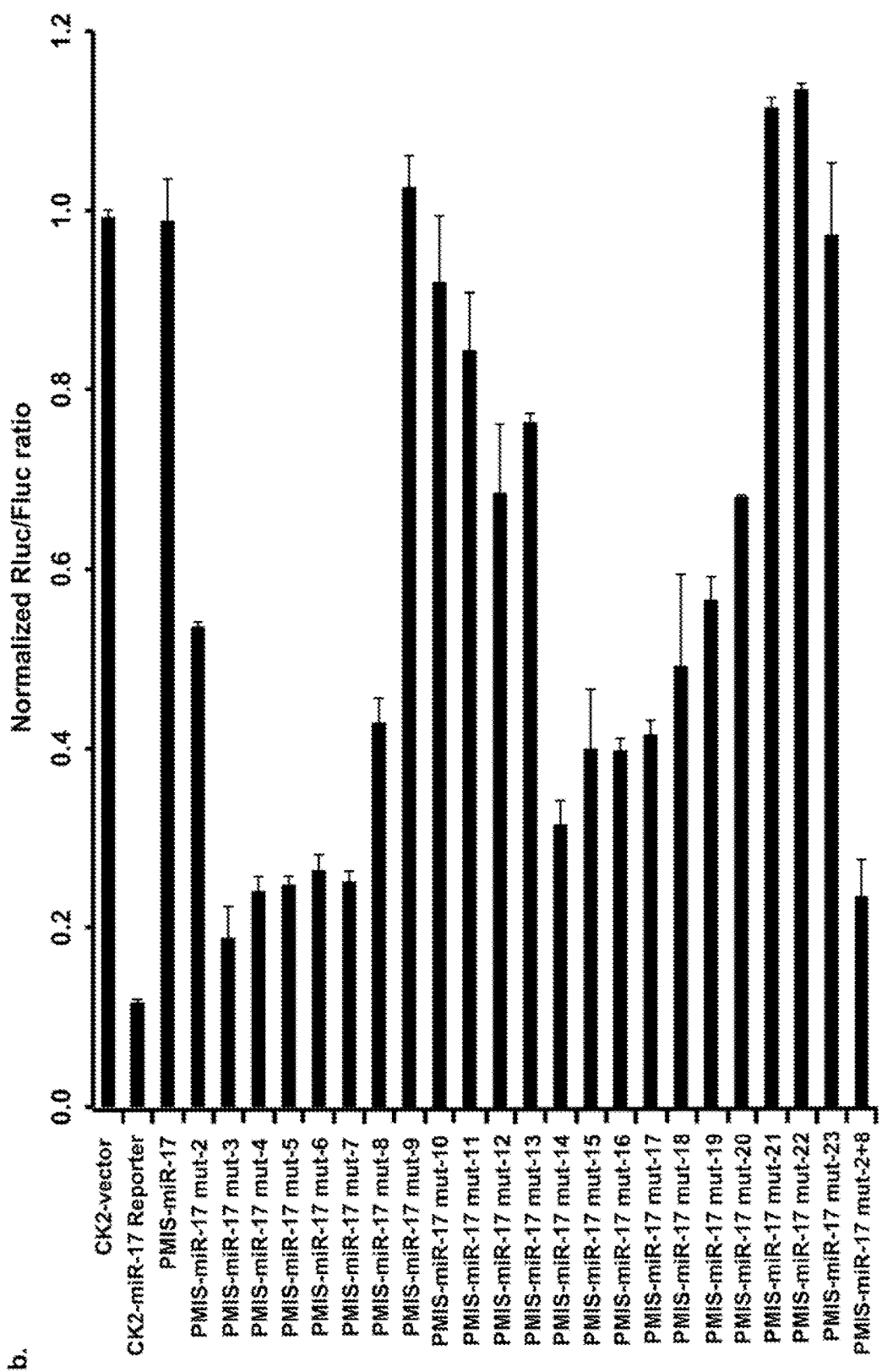
FIG. 3. Specificity of miR inhibitors. a) Sequence of miR-17 inhibitor and specific mutations to test function. The numbers indicate the mutated ribonucleotide (bold and in caps) and the "auca" sequence in the middle of the inhibitor sequence eliminates a perfect match. The seed sequence of the mature miR-17-5p is in bold as is the antisense sequence to the seed sequence in PMIS-miR-17 FIG. 3a discloses SEQ ID NOS 3 and 26-49, respectively, in order of appearance. b) Ribonucleotide mutation effects on miR inhibitor efficiency. Normalized Rluc to Fluc ratio of miR reporter vector without miR-17 binding site was set as 100 percent. The PMIS-miR-17 inhibitor mutants were co-transfected with miR reporter vector containing a miR-17 binding site into HEK 293FT cells. Rluc and Fluc activity was measured 48 hours after transfection.

Specific nucleotides were mutated in PMIS-miR-17 (FIG. 3a) and tested for function using the dual luciferase assay as in FIG. 1d. As expected, a single mutation of the inhibitor corresponding to the seed sequence (nts 2-8, mut-2 to 8) of miR-17 almost completely eliminated its effects (FIG. 3a,b). Another region important for miR inhibitor function corresponds to nts 12-20, (mut-12 to 20) (FIG. 3a,b). Other nucleotide changes do not significantly impair miR inhibitor function. As expected changing two nucleotides corresponding to the seed region (mut-2+8) has additional additive effects (FIG. 3a,b).

miR-200 Family Knockdown by a Single miR Inhibitor Plasmid

We hypothesized that one miR inhibitor could inhibit different members of the same miR family. To test this hypothesis, cells were transfected with the miR reporter luciferase construct, the associated miR that binds to the target in the luciferase construct and the miR inhibitors or empty vector. The miR-200 family has two subfamilies, miR-200a-3p/141-3p and miR-200b-3p/200c-3p/429-3p (FIG. 4a). These two subfamilies have one nucleotide difference (underlined) in their seed regions. PMIS constructs for miR-200a or -141 (PMIS-miR-200a or PMIS-miR-141) inhibited the miR-200a/141 subfamily but not the miR-200b/200c/429 subfamily (FIG. 4b,c). PMIS for miR-200b, -200c or -429 inhibited the miR-200b/200c/429 subfamily efficiently but not the miR-200a/141 subfamily (FIG. 4d, e, f). However, the inhibitor to miR-429 was not as effective at knocking down miR-200c expression compared to inhibitors 200a and 200b, due to flanking sequence divergence of miR-429 (and the inhibitor). To inhibit the miR-200 family, PMIS-miR-200b-200a was constructed and contains a U6 promoter followed by a miR-200b inhibitor, a second U6 promoter followed by miR-200a inhibitor (FIG. 1c). This construct allows for the expression of multiple miR inhibitors from one plasmid to inhibit the entire miR-200 family (FIG. 4g).

miR-200 Inhibitor Induces an Epithelial to Mesenchyme Transition (EMT) in MDCK Cells Over expression of miR-200 promotes a mesenchymal to epithelial transition (MET) in MDCK-Pez cells and conversely inhibition of miR-200 causes EMT in MDCK cells[37]. To test if the PMIS-miR-200 inhibits miR-200 function in vitro and promotes EMT, a stable MDCK cell line was made that expresses PMIS-miR-200a-200b. Immunofluorescence of the epithelial marker E-cadherin confirmed that MDCK cells underwent EMT after expression of PMIS-miR-200a-200b.

The PMIS Inhibits Different Types of miRs and siRNA

Figure 7:
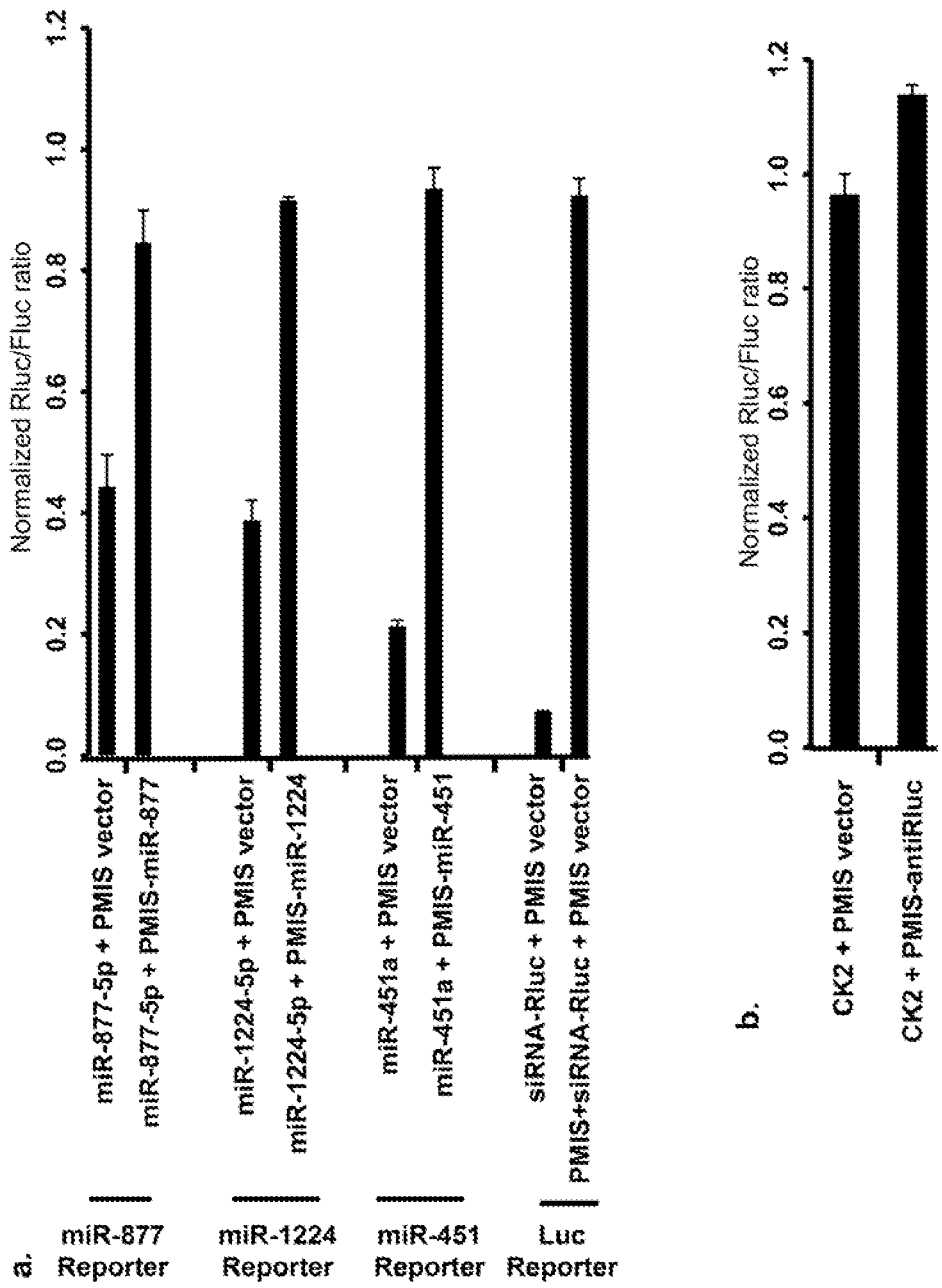
FIG. 7. Efficiency of PMIS-miR inhibitor targeting non-canonical miRs. a) Efficiency of PMIS-miR inhibitors targeting intronic miRs that bypass Drosha processing miR-877-5p and miR-1224-5p, Dicer-independent miR-451a and in-vitro transcribed siRNA. PMIS-miR inhibitor targeting Rluc mRNA served as a control. Rluc and Fluc were assayed as in previous figures. b) As an additional control PMIS-anti-Rluc had no effect on luciferase expression and activity.

In addition to the canonical miR biogenesis pathway, there are other types of miRs that do not require Drosha or Dicer to process them for functionality. To test whether the PMIS inhibits non-canonical miRs, inhibitors were made to two miRs that do not require Drosha (miR-877-5p and miR-1224-5p) and one that does not require Dicer (miR-451a). The miR inhibitors inhibited both miRs (FIG. 7a). siRNAs are different from miRs in that they do not require Drosha and Dicer processing for function. However, both siRNAs and miRs load into a functional RNA-induced silencing complex (RISC). To test whether the PMIS also works on siRNAs, we designed a siRNA to luciferase mRNA. The PMIS to this siRNA efficiently blocks siRNA function (FIG. 7a). As a negative control, this PMIS does not knockdown luciferase activity by itself (FIG. 7b). Thus, the PMIS works specifically on all miRs and siRNAs.

miR Inhibitor Associates with Dicer and Argonaute

To determine whether the PMIS constructs were bound by Argonaute (AGO), 293 cells transduced with PMIS vector only, PMIS-miR-200c or PMIS-miR-17 were subjected to immunoprecipitation (IP) assays using either IgG (control) or AGO antibodies. After IP the complexes were washed and denatured and PCR was performed using primers for PMIS-miR-17. The complexes containing endogenous miR-17 and PMIS-miR-17 were pulled-down by the AGO antibody (FIG. 5a, lane 6). A similar IP used the Dicer antibody to pull-down the inhibitor complex and Dicer was associated with PMIS-miR-17 (FIG. 5b, lane 6). In addition, proteins were pulled down that associated with the miR inhibitor using biotin in vitro transcribed RNA and incubated with cell lysates and probed for Dicer and AGO binding by Western blot. The PMIS associates with Dicer and AGO and this association decreased when the miR inhibitor lost its double stranded RNA structure (FIG. 5c).

To test whether Dicer was required for PMIS function, siRNA was used to knockdown Dicer (FIG. 5d). The PMIS inhibits siRNA, which targets the luciferase gene (Rluc) and siGFP has no effect, used as a control (FIG. 5e). However, after knocking down Dicer with siRNA the miR inhibitor to siRNA-Rluc has no effect on inhibiting the activity of the siRNA to Rluc (FIG. 5e). A proposed working model is shown for the PMIS-miR-inhibitor miR complex (FIG. 5f).

The PMIS is Relatively Stable in Cells

To determine the relative stability of the miR inhibitor, cells were transduced with lentivirus expressing PMIS-miR-200b. The cells were seeded at identical densities into 6-well plates and after 24 hours they were subjected to actinomycin D (5 ng/ml) treatment for the indicated time (days). The PMIS showed no decrease in transcript stability after 7 days of treatment, compared to beta-actin. However, 28S, 18S and 5S RNAs were all degraded after 5 days of treatment with actinomycin D. Because the average miR half-life is ~5 days the PMIS appears to be more stable than miRs allowing them to remain functional in the cell[38].

Analyses of Gene Regulation by PMIS-miR-17

Figure 8:
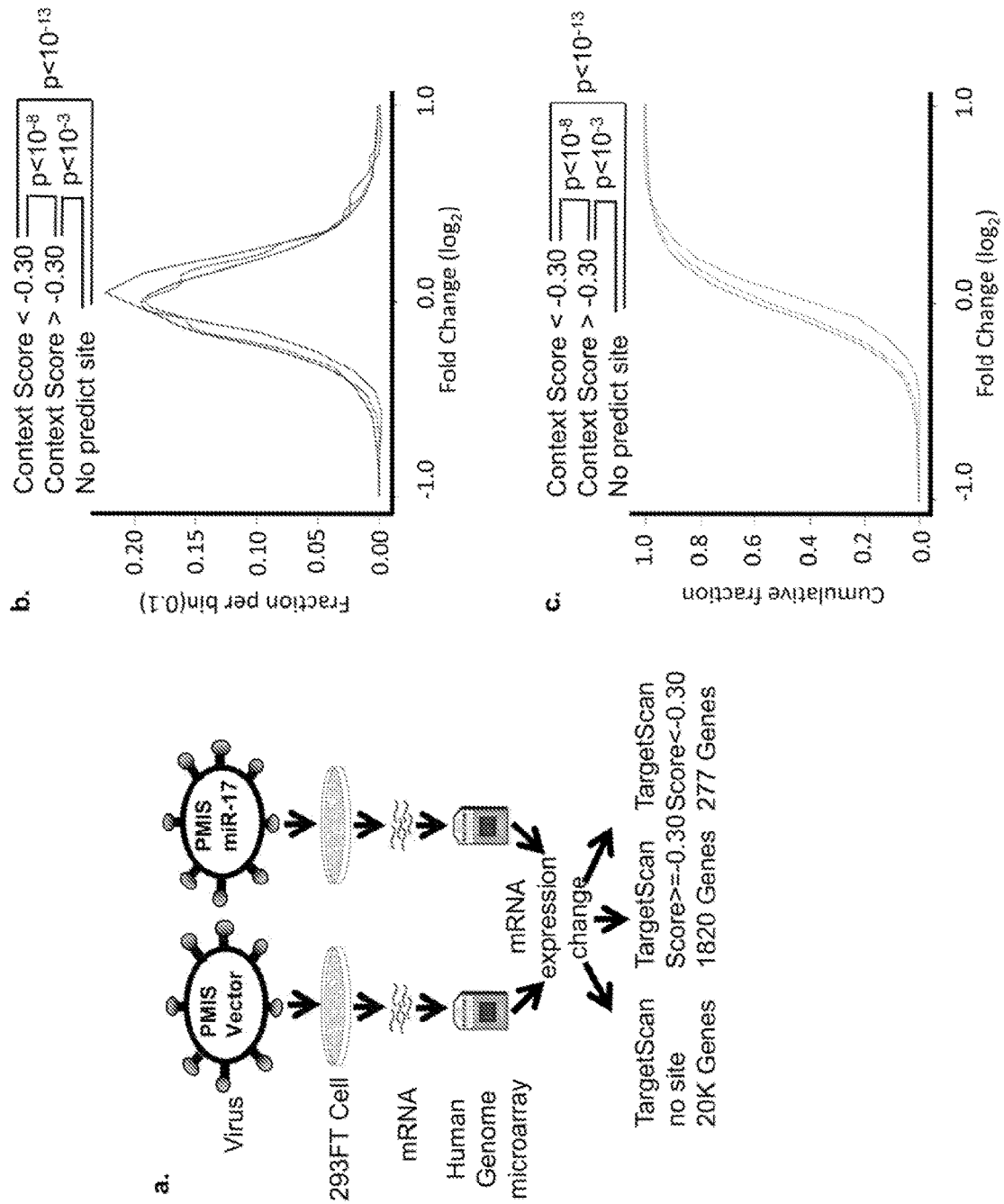
FIG. 8. Genome wide analyses of PMIS-miR-17 function. a) Experiment design for the whole genome wide analysis of mRNA change after transduction with PMIS-miR-17. b, c) Changes in abundance of mRNAs in PMIS-miR-17 expressing 293 cells were monitored by microarrays. TargetScan was used to predict miR-17 targets. We further separate miR-17 targets into two groups, one with context+ score lower than −0.30 and the other with context+ score higher than −0.30. Distributions of changes (0.1 unit bins) for mRNA UTRs containing no site in black line, site with score higher than −0.30 in red line and site with score less than −0.30 in blue line. Up-regulation from UTRs with context+ score less than −0.30 was significantly more than that from UTRs with no site ($p<10^{-13}$, one-sided K-S test). Comparisons between UTRs with context+ score less than −0.30 versus context+ score higher than −0.30, context+ score higher than −0.30 versus no site were also significant ($p<10^{-8}$, $p<10^{-3}$, respectively).

A genome-wide analyses of mRNA changes was performed after transduction with PMIS-miR-17 in 293 cells. A schematic of the experimental design is shown and TargetScan was used to predict miR-17 targets (FIG. 8a). The miR-17 targets were separated into two groups, one with a context+ score lower than −0.30 and the other with a context+ score higher than −0.30. Distributions of changes (0.1 unit bins) for mRNA UTRs containing no site (black line), site with a score higher than −0.30 (red line) and site with a score less than −0.30 (blue line) (FIG. 8b, c). Up-regulation from UTRs with context+ score less than −0.30 was significantly more than that from UTRs with no site ($p<10^{-13}$, one-sided K-S test).

Comparisons between UTRs with context+ score less than −0.30 versus context+ score higher than −0.30; context+ score higher than −0.30 versus no site were also significant ($p<10^{-8}$ and $p<10^{-3}$, respectively)(FIG. 8b, c).

Figure 9:
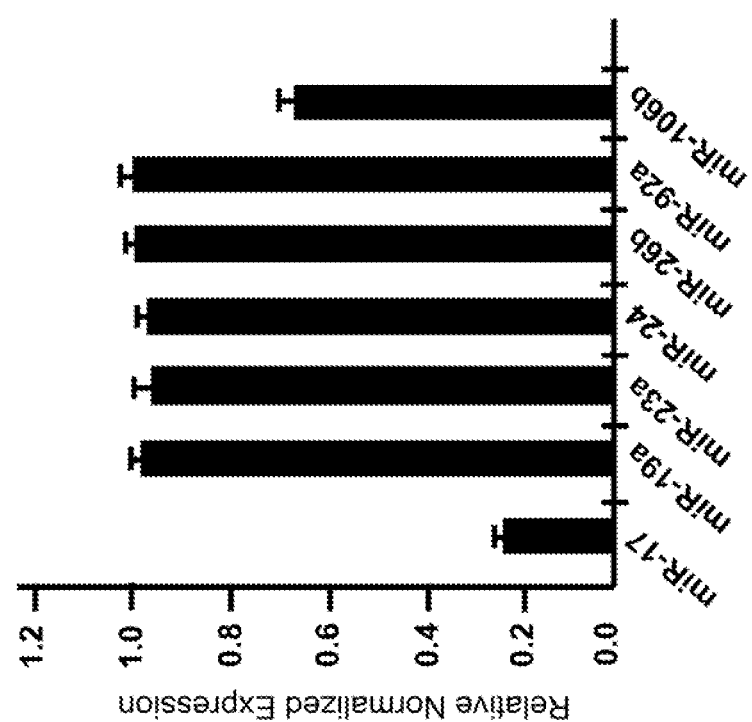
FIG. 9. PMIS-miR-17 specifically targets miR-17. 293 cells were transduced with PMIS-miR-17, total RNA harvested and randomly selected miR expression was analyzed by real time PCR using Taqman probes (N=3).

To determine if PMIS-miR-17 inhibited other miRs in cells, 293 cells were transduced with the lentiviral PMIS miR-17 and randomly selected miRs were profiled by RT-PCR (Taqman probes, Applied Biosystems). PMIS miR-17 was specific for the inhibition of miR-17-5p and miR-106b-5p (FIG. 9).

PMIS Inhibits miRs During Mouse Development

The PMIS was designed as a pronuclear injected construct to create transgenic mice that stably express the miR inhibitors. This PMIS has an antirepressor element upstream of the mouse U6 promoter followed by a miR inhibitor, a second U6 promoter followed by different miR inhibitor, a scaffold-attached region (SAR) and polyA site (FIG. 10).

Figure 10:
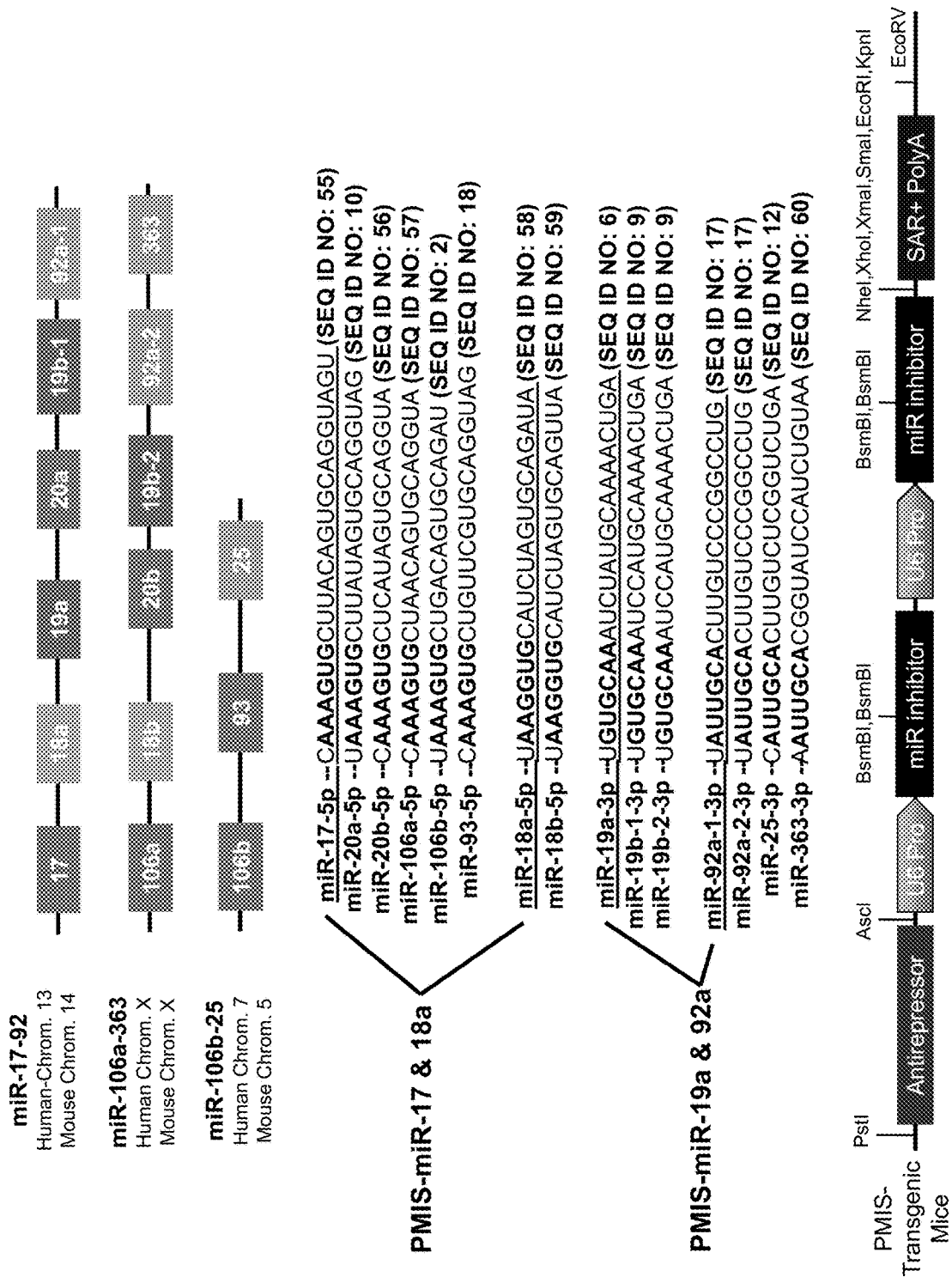
FIG. 10. Schematic of the miR-17-92, miR-106a-363 and miR-106b-25 clusters. The location and organization of the miR clusters are shown in the top panel. The middle panel shows the sequence similarities and differences between the miRs. PMIS-miR-17 and 18a were derived from miR-17-5p and miR-18a-5p, respectively. PMIS-miR19a and 92a were derived from miR-19a-3p and miR-92a-1-3p, respectively. The structure of the construct used for pronuclear injection is shown at bottom of figure.

The top panel of FIG. 10 shows the location of three microRNA clusters in the human and mouse genomes. The microRNAs with identical color coding have identical sequences and function, although they are expressed on different chromosomes. This is a very important point as the present PMIS microRNA inhibitor can target identical microRNA sequences and microRNAs even though they are expressed on different chromosomes. Genetically, it is impossible to knockout these microRNAs or, more important, therapeutically target all of these microRNAs with conventional known reagents. The middle panel of FIG. 10 shows the actual sequences of the color coded microRNAs showing identical seed sequences (sequences that directly base pair with the gene sequence to inhibit gene expression). PMIS-miR-17 & 18 construct targets and inhibits the miRs indicated (e.g., PMIS-miR-17 inhibits the six blue color miRs, while PMIS-miR-18 inhibits the green color miRs) both miR inhibitors are expressed on one plasmid (e.g., PMIS-miR-17 & 18). The same is true for PMIS-miR-19a and 92a, where the underlined miRs are targeted and share the same sequence with others in the group. The bottom panel (PMIS-Transgenic Mice) shows the construct placed into our vector that provides specific and stable expression of the PMIS constructs in transgenic mice (the first of its kind). This linearized DNA fragment is pronuclear injected into mouse blastocysts to generate new mice expressing the PMIS.

The miR-17-92 null mice have been reported[36, 39, 40], and we made PMIS mice targeting these miRs as proof of principle. Because the miR-17-92$^{null}$ mice are perinatal lethal, two PMIS constructs PMIS-miR-17-18a and PMIS-miR-19a-92a were pronuclear injected to make transgenic (TG) mice (FIG. 10, underlined sequence). These 4 miR inhibitors target the 4 seed regions shared among the miR families (FIG. 10). Multiple founders were generated and PMIS-miR-17-18a #6 demonstrated 95% knock down of miR-17 and 86% knock down of miR-18a by real time PCR (FIG. 6a). Multiple founders for PMIS-miR-19a-92a showed decreased miR expression, PMIS-miR-19a-92a-E7 inhibited miR-19a at 95% and miR-92a at ~65% (FIG. 6b). Founders PMIS-miR-17-18a #6 and PMIS-miR-19a-92a-E7 were established and these mice were crossed to generate the PMIS-miR-17-92 TG mice. The PMIS-miR-17-18a and PMIS-miR-19a-92a mice are viable, however approximately 25% have craniofacial defects that cause neonatal lethality. The PMIS-miR-17-92 mice are perinatal lethal similar to the miR-17-92$^{null}$ mice. PMIS-miR-17-92 embryos (E18.5) are smaller than wild type (WT) embryos with reduced body weight as reported for the miR-7-92$^{null}$ mice (FIG. 6c, d)$^{36, 40}$. These mice also have small lungs (FIG. 6e).

miR-17-92 Expression is Inhibited in the PMIS-miR-17-92 Mice

Mouse tissues from E18.5 PMIS-miR-17-18, PMIS-miR-19-92 and PMIS-miR-17-92 TG mice were analyzed for miR expression. To analyze large miR sets, the Qiagen protocol for miR detection was used to determine miR expression profiles (primers shown in Table 1).

TABLE 1

Primers used for qRT-PCR of mature miRs in transgenic mice.

| Primer | Sequence | SEQ ID NO: |
|---|---|---|
| mmu-miR-106a-5p MIMAT0000385 | CAAAGUGCUAACAGUGCAGGUAG | 1 |
| mmu-miR-106b-5p MIMAT0000386 | UAAAGUGCUGACAGUGCAGAU | 2 |
| mmu-miR-17-5p MIMAT0000649 | CAAAGUGCUUACAGUGCAGGUAG | 3 |
| mmu-miR-18a-5p MIMAT0000528 | UAAGGUGCAUCUAGUGCAGAUAG | 4 |
| mmu-miR-18b-5p MIMAT0004858 | UAAGGUGCAUCUAGUGCUGUUAG | 5 |
| mmu-miR-19a-3p MIMAT0000651 | UGUGCAAAUCUAUGCAAAACUGA | 6 |
| mmu-miR-19b-1-5p MIMAT0017065 | AGUUUUGCAGGUUUGCAUCCAGC | 7 |
| mmu-miR-19b-2-5p MIMAT0017010 | AGUUUUGCAGAUUUGCAGUUCAGC | 8 |
| mmu-miR-19b-3p MIMAT0000513 | UGUGCAAAUCCAUGCAAAACUGA | 9 |
| mmu-miR-20a-5p MIMAT0000529 | UAAAGUGCUUAUAGUGCAGGUAG | 10 |
| mmu-miR-20b-5p MIMAT0003187 | CAAAGUGCUCAUAGUGCAGGUAG | 11 |
| mmu-miR-25-3p MIMAT0000652 | CAUUGCACUUGUCUCGGUCUGA | 12 |
| mmu-miR-363-3p MIMAT0000708 | AAUUGCACGGUAUCCAUCUGUA | 13 |
| mmu-miR-363-5p MIMAT0017076 | CAGGUGGAACACGAUGCAAUUU | 14 |
| mmu-miR-92a-1-5p MIMAT0017066 | AGGUUGGGAUUUGUCGCAAUGCU | 15 |
| mmu-miR-92a-2-5p MIMAT0004635 | AGGUGGGGAUUGGUGGCAUUAC | 16 |
| mmu-miR-92a-3p MIMAT0000539 | UAUUGCACUUGUCCCGGCCUG | 17 |
| mmu-miR-93-5p MIMAT0000540 | CAAAGUGCUGUUCGUGCAGGUAG | 18 |

Figure 11:
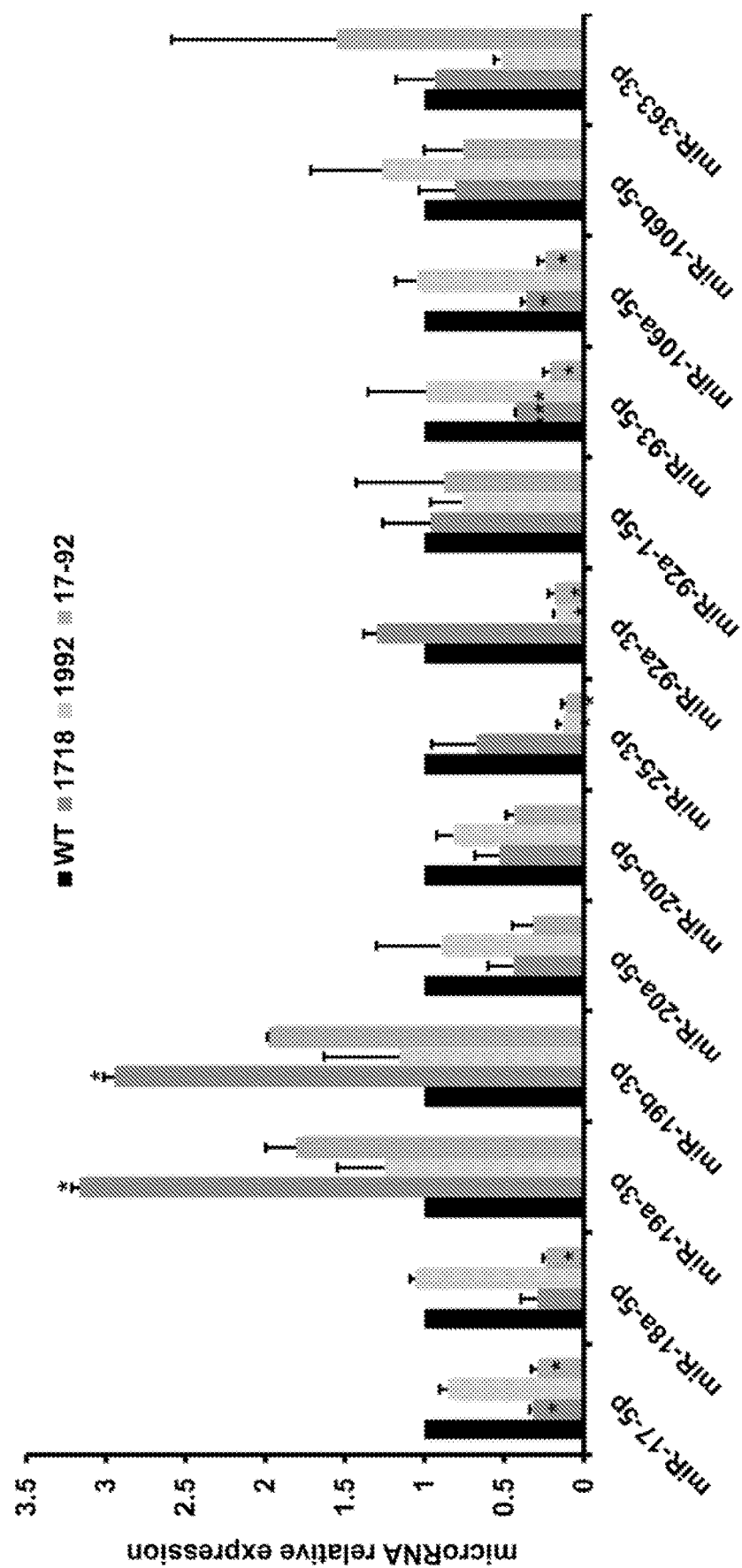
FIG. 11. miR expression levels in PMIS-miR-17-18a, PMIS-miR-19a-92a and PMIS-miR-17-92 TG mice. Total RNA was harvested from E18.5 mice heads and subjected to miR expression analyses as per manufacturer's suggestion (Qiagen). miR expression is calculated as ΔΔCT after normalization to control primers. All data was compared to WT mice (N=2, 2 different mice and qPCR performed in triplicate for each mouse; *, $p<0.05$).
Figure 12:
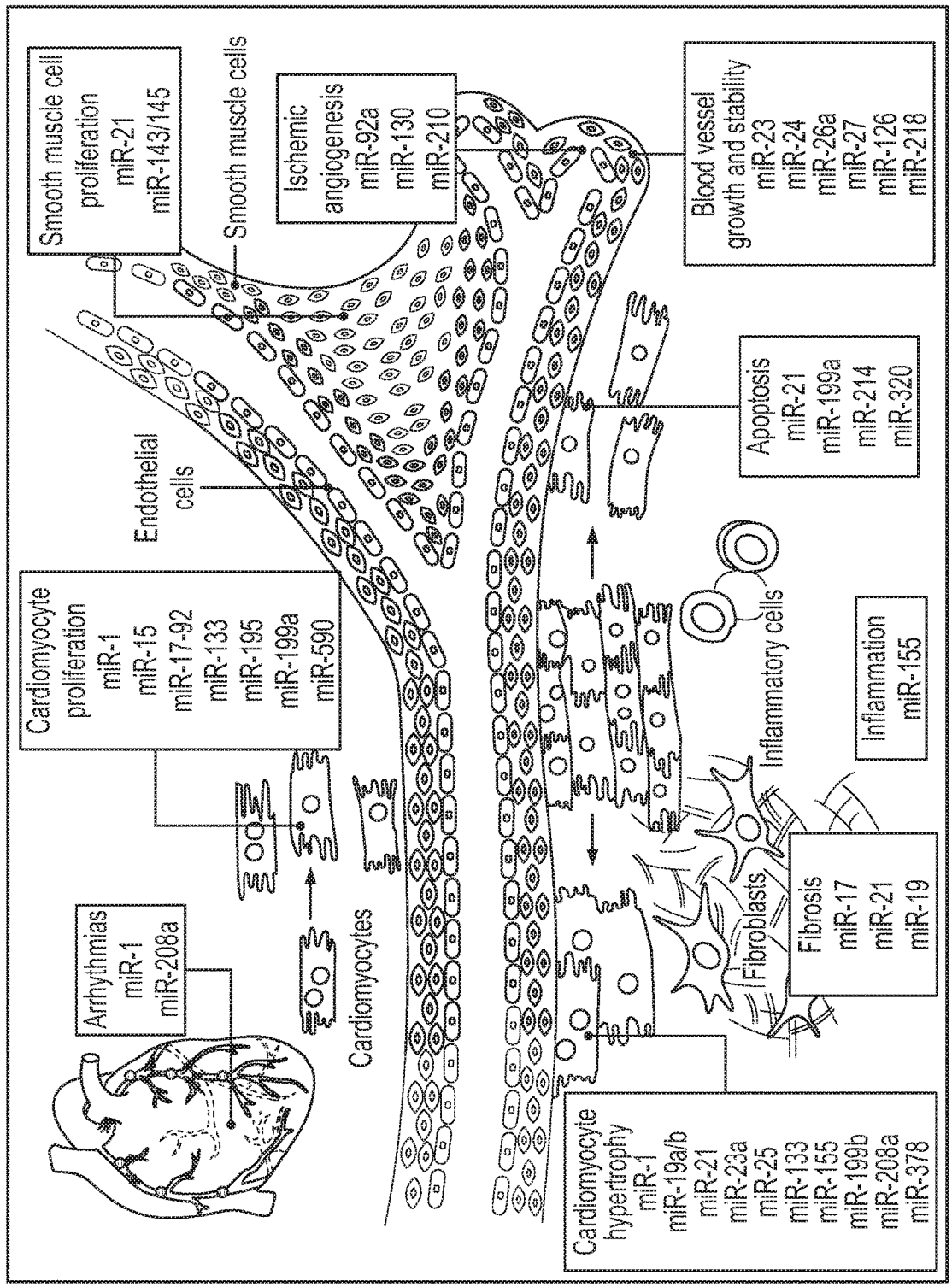
FIG. 12 miRNAs in cardiovascular disease.

Specific miR expression associated with PMIS-miR-17-18 and PMIS-miR-19-92 mice were decreased while the complete miR-17-92 family, except for miR-19a and -19b were inhibited in the PMIS-miR-17-92 mice (FIG. 11). The increase in miR-19a and -19b in the PMIS-miR-17-18 mice may indicate a new mechanism where miR-17 and/or -18a negatively regulate the expression of miR-19a and -19b, which reside in the same cluster. Further experiments are underway to determine the specific expression mechanism. Furthermore, miR-92a-1-5p is an internal control and not targeted by the inhibitor system.

Craniofacial Defects in the PMIS-miR-17-92 Mice

The miR-17-92$^{null}$ mice have defects associated with Feingold syndrome including microcephaly$^{40}$. Bone and cartilage development was analyzed in E18.5 skulls of PMIS-miR-17-18 mice, PMIS-miR-19-92 mice and the combined PMIS-miR-17-92 mice compared to wild type mice. The PMIS-miR-17-92 mice have microcephaly represented as a shortening of the anterior-posterior axis and an overall reduction in size with a decrease in ossification of the parietal (P) and interparietal (IP) bones. Interestingly, the PMIS-miR-17-18 mice have a normal anterior-posterior axis with normal ossification however the skull width is slightly narrower than WT mice. The PMIS-miR-19-92 mice have a reduced anterior-posterior axis similar to the PMIS-miR-17-92 mice and reduced width of the skull in the dorsal view. These two PMIS mice show separation of the effects of the miR-17-92 cluster where miR-17 and -18 control skull width and miR-19-92 control width and anterior-posterior axis growth, but normal ossification.

The PMIS-miR-17-92 mice (E18.5) have a cleft palate as shown for the miR-17-92$^{null}$ mice$^{39}$. In the miR-17-92$^{null}$ the palate shelves elevate and adhere with the nasal septum but do not form the secondary palate and this was observed in the P0 PMIS-miR-17-92 mice as well (data not shown). However, several mice also showed a lack of or incomplete palate shelf fusion with the nasal septum.

Skeletal Defects are Associated with Disrupted miR-17-92 Activity

The PMIS-miR-17-92 mice (E18.5) were stained with alcian blue and alizarin red to detect cartilage and bone, respectively. The PMIS-miR-17-92 mice lack the lesser horn of hyoid, greater horn of hyoid, thyroid cartilage and cricoid cartilage. The sternum is smaller and these mice have fusions of the first three cervical vertebrae as previously shown (data not shown)$^{40}$. Interestingly, the PMIS-miR-17-92 mice lack the processus angularis.

A unique aspect of the PMIS is its ability to target specific miRs within a cluster. Analyses of PMIS-miR-17-18 mice show the thyroid cartilages compared to WT. While there is dyssymphysis of the 1$^{st}$ and 2$^{nd}$ cervical vertebrae in this mouse they are not fused as shown for the miR-17-92$^{null}$ mouse$^{40}$. The PMIS-miR-19-92 mice have normal thyroid cartilages with dyssymphysis of the 1$^{st}$ and 2$^{nd}$ cervical vertebrae. The PMIS-miR-17-92 mice have an almost complete loss of thyroid cartilages, loss of the processus angularis and dyssmphysis and fusion of the C1 and C2 vertebrae. However, miR-19 and -92 appear to regulate thyroid and cervical vertebrae development (without fusion of the vertebrae) and mandible and head size (microcephaly). This phenotype is repeated in the PMIS-miR-17-92 mice, however these mice have fusion of the cervical vertebrae and a loss of the processus angularis and microcephaly.

Digit Formation is Affected in the PMIS-miR-17-92 Mice

The PMIS-miR-17-92 E18.5 embryos show abnormal hand and foot development similar to the miR-17-92$^{null}$ embryos$^{40}$. The PMIS-miR-17-18 embryos display hypoplastic digits but otherwise normal morphology of the right hand. PMIS-miR-19-92 embryos reveal normal structures, size and endochondral ossification, however the falciform carpal is missing. The PMIS-miR-17-92 embryos have a complete absence of the mesophalanx of the third, fourth and fifth digits similar to miR-17-92$^{null}$ embryos.

The bones of the left foot and digits appear to be normal in the PMIS-miR-17-18 and PMIS-miR-19-92 embryos compared to WT, however, the second phalange of the 1$^{st}$ metatarsal is missing or deformed in the PMIS-miR-17-92 embryos.

Discussion miRs are essential regulators of gene expression and critical for normal embryonic development, tissue morphogenesis, cellular functions such as metabolism and are associated with cancer cell types. However, our knowledge of the full aspects of miR function during development remains fragmentary due to the limited availability of experimental tools to knockdown or knockout miRs in vivo.

Several approaches have been reported to knockdown miRs in adult mice but not during embryonic development. One method reported using the TuD system delivered using recombinant adeno-associated virus (rAAV) injected into adult mice[41]. The rAAV expressing anti-miR-122 TuD reduced serum cholesterol by >30% for 25 weeks in mice. A second method used lentiviral vectors to express miRT sequences (sponges, decoys, antagomirs) to miR-223 in transduced bone marrow stem and progenitor cells transplanted into mice recipients[42]. While both systems inhibited miR activity for their specific miR target, there are limitations to both systems. Furthermore, both methods have dose response problems and neither have the ability to function as a transgene for developmental studies and long term knockdown of multiple miR family members. A third method used a transgenic mouse expressing a sponge to bind miR-183 and these mice demonstrated retina defects[43]. These methods are critically advancing our knowledge of miR function in vivo and provide a wealth of knowledge on miR function.

Our findings advance these methods by using a novel RNA structure that inhibits miR function in vivo and can target multiple miRs with the same seed sequence. The PMIS system is more efficient than the sponge or antagomir sequences. The PMIS was designed independently of the TuD system and incorporates a unique RNA secondary structure that facilitates in vivo anti-miR function. Both the TuD and PMIS have similar anti-miR binding sequences including a 4 nucleotide bulge region[41]. We demonstrate that both Ago and Dicer bind to the PMIS and we speculate that these interactions stabilize the miR-Inhibitor complex. Dicer is not required for RISC loading in mammals but its interaction with the PMIS may facilitate the inhibitor's function[44]. The PMIS is stable in cells and the targeted miRs are degraded as seen in PMIS mice.

We demonstrate an effective system to target miRs and miR clusters in mice using a transgenic approach. The PMIS can dissect the function of specific miRs expressed in miR clusters during development. This technique is cost effective and does not required time consuming and costly gene targeting mutagenesis as shown for the miR-17-92, miR-106b-25 and miR-106a-363 target deletions[36]. The PMIS-17-92 mice demonstrate similar phenotypes as the miR-17-92 family knockout mice, demonstrating the efficiency of the PMIS system[36]. Furthermore, using specific PMIS constructs the function of each miR family member can be analyzed during development and in cells. It can be used in viral systems to create stable PMIS expressing cells and tissues in culture, or in transgenic mice to study miR function. The PMIS can be delivered using nanoparticles, viruses and lipid-based systems to treat cancers with aberrant miR expression or to protect cells and tissues from aberrant gene expression. There is great utility for this system as a therapeutic reagent as the PMIS is extremely specific for each miR. Because this is a plasmid-based miR inhibitor it is easy and inexpensive to use without reapplication in cells that is required for other modified antisense oligonucleotide systems.

Methods

Construction of miR Reporter, Expression and Inhibitor Plasmids

To anneal oligos, oligos were heated at 70° C. for 10 minutes and then slowly cooled to room temperature. For ligation, annealed oligos were phosphorylated by T4 polynucleotide kinase (NEB) first and then ligated into vectors using the quick ligation kit (Roche) as per instructions. To construct miR reporters, one perfect match miR binding site was ligated after the Renilla luciferase gene in psiCHECK2 vector (Promega, dual reporter system) digested with NotI and XhoI. To construct a miR expression plasmid, miR genes were PCR amplified that include approximately 100 bp upstream and 100 bp downstream sequence flanking the approximately 80bp stem loop sequence. The PCR product was ligated into pSilencer 4.1 vector (Ambion) digested by BamHI and HindIII. To construct different designs of miR inhibitors for miR-17, we annealed and ligated the miR-17 binding site with a central bulge flanked by different sequences into pLL3.7 vector (Addgene) digested with HpaI and XhoI. To construct the miR inhibitor clone vector, we replaced the miR-17 binding site with two BsmBI sites in the most effective inhibitor design. AscI and PmeI sites were inserted between ApaI and XbaI sites before the U6 promoter. A SmaI site was inserted before XhoI after the polIII terminator. This vector is termed pmiRI for plasmid of miR inhibitor. After digestion by BsmBI, pmiRi can be used to clone different miR inhibitors into it after annealing and ligation of different miR binding sites with a central bulge. To link two different miR inhibitors, one plasmid is digested by AscI and SmaI to release a fragment about 500 bp; this fragment can be ligated into another miR inhibitor digested by AscI and PmeI. Plasmid constructs are shown in FIG. 1C for cell transductions and FIG. 9 for transgenic mice. Sponge reporter was made by inserting 6 tandem binding sites for miR-17 into the psiCHECK2 vector.

Cell Culture, Transfection and Luciferase Assays

HEK293FT (Invitrogen) and MDCK (ATCC) cells were cultured in DMEM supplemented with 10% fetal bovine serum (FBS) and penicillin/streptomycin. HEK293FT cells are plated the day before transfection. 20 ng of miR reporter and 200 ng of miR inhibitor are co-transfected into each well of 12 well plates using Fugene6 (Roche). For exogenous miR expression, 200 ng miR expression plasmid was transfected into cells. The Dual-Luciferase Reporter assay (Promega) was performed 48 hours after transfection as per instructions. siRNA targeting Dicer (aaggacgguguucuuggucaac (SEQ ID NO: 19) and cugcuugaagcagcucuggauc (SEQ ID NO: 20)) and GFP (aggacgacggcaacuacaagac (SEQ ID NO: 21)) were in vitro transcribed and transfected into cells as described[45].

Stability Assay of the PMIS Constructs

MG-63 cells were transduced with PMIS-miR-200b lentivirus, after 48 hours, cells were seeded in 6-well plates at the same density (30-40%) with 0.1% DMSO in DMEM medium. After 24 hours, cells are treated with actinomycin D at the concentration of 5 ng/ml (marking the time point as day 0). Cells were harvested at different time points and total RNA isolated using Qiagen miRNeasy Mini Kit. cDNAs were made by using TaKaRa PrimeScript RT Master Mix kit. The PCR cycles were as follows: initial denaturation at 95° C. for 1 min, 94° C. for 30 s, annealing at 60° C. for 30 s, and extending at 72° C. for 30 s. The PCR Primers were as follows: For human beta actin primers were 5'-CATGTACGTTGCTATCCAGGC-3' (SEQ ID NO: 22) and 5'-CTCCTTAATGTCACGCACGAT-3' (SEQ ID NO: 23); for PMIS-miR-200b primers were 5'-CTAATCATCATTACCAATCAGACAGTATTA-3' (SEQ ID NO: 24) and 5'-GTCAGCTCTTAGTATTCATGAGATG-3' (SEQ ID NO: 25) Total RNA from each time point and PCR products were detected in agarose gels. All PCR products were confirmed by sequencing.

Lentivirus Production and Transduction

For lentivirus production, 6 cm dish of HEK293FT cell were transfected with 2.8 µg of psPAX2, 1.9 µg of pMD2.G and 4.5 µg of miR inhibitor or control plasmid using Fugene HD (Roche). Supernatants were collected and passed through 0.45 μm filter 28 hours after transfection. To concentrate virus preparations, 40 ml of supernatant was centrifuged at 26,000 rpm for 2 hours at 4° C. Pellets were resuspended in 100 μl of DMEM at 4° C. overnight. For lentivirus transduction of MDCK cells, 1×10$^5$ cells were seeded in 6 cm dish immediately before addition of 30 μl of concentrated virus. MG-63 cells used for actinomycin D experiments were subcultured and transferred to 6-cm dishes at 30% confluence. Virus was added immediately after plating and cultured for 2 weeks with media change every 2-3 days. Puromycin was added for selection and stable PMIS-miR-17 expressing cells were used to analyze the stability of the PMIS.

Fluorescence Activated Cell Sorting

Flow Cytometry Facility of the University of Iowa preformed cells sorting using the Becton Dickinson Aria II. Cell suspensions were placed in a 12×75 mm test tube with the final cell concentration between 5×10$^6$ and 30×10$^6$ cells per ml. Prior to sorting, cells are filtered through 70 μm nylon mesh (Falcon 352350). Cells are then sorted by GFP and collected at 37° C. into 12×75 mm test tube in DMEM medium with 10% FBS. The cells are then cultured.

Realtime PCR, Western Blot and Immunofluorescence

For quantification of mature miRs, Taqman probe (Applied Biosystems) were used as per instructions. Small RNA U6B served as a control. For quantification of miR primary transcripts, iQ SYBR Green Real-Time PCR Supermix (BioRad) was used as per instructions. Beta-actin mRNA served as a control. For Western blots, approximately 20 μg of cell lysates were loaded and ran in SDS-PAGE. Proteins were transferred to PVDF filters (Millipore), immunoblotted using antibodies and detected by ECL reagents (GE Healthcare). The dilution of Dicer antibody (Abcam) was 1 to 500. Argonaute 2 antibody (Cell Signaling) was 1 to 1000. For immunofluorescence, cells were fixed by cold acetone, blocked with 10% serum of secondary antibody, incubated with primary antibody for 1 hour and detected by secondary antibody fluorescence. Cells were counterstained with DAPI.

Real Time PCR of Mature miRs from E18.5 Mouse Heads

E18.5 embryos were harvested and heads were used for total RNA isolation. Total RNA including miR from mouse tissues was prepared using the miRNeasy Mini Kit (Qiagen). Quantitative real-time PCR (qPCR) analysis of selected miRs was performed using TaqMan microRNA assay probes (Applied Biosystems), and U6B probe (Applied Biosystems) was used as a reference for normalization. miR-17-92 expression analyses in mouse tissues was performed as follows; cDNA for mature miR quantification were made by using miScript PCR Starter Kit (Qiagen) and quantitative PCR of mature miRs were done with SYBR Green PCR Kit (Qiagen). Primers for detected mature miRs are listed in Table 1.

Northern Blot Assay

For miR northern blot, 5'-end DIG-labeled mercury LNA miR detection probes for miR-17 and U6 from EXIQON were used according to manufacturers' instructions. Briefly, total RNA including miR from cells stably expressing PMIS vector or PMIS-miR-17 was extracted. 10 micrograms of total RNA were loaded on a denaturing 12% polyacrylamide gel. After transfer, membrane was hybridized with 5'-end DIG-labeled mercury LNA miRNA detection probes.

Immobilization of RNA on Agarose Beads and Pull Down Assay miR inhibitor RNA with and without flanking double strand RNA was synthesized in vitro by T7 RNA polymerase and DNA oligonucleotide templates. These RNA were biotinylated using 3' end biotinylation kit (Thermo Scientific). Biotinylated RNAs were incubated with streptavidin-conjugated agarose beads for 1 hour at 4° C. HEK293FT cell were collected and sonicated with protease inhibitor on ice. The cell lysate were pre-cleared with beads only. After preclearing, cell lysate were incubated with RNA immobilized on the streptavidinbeads and rotated for 12 hours at 4° C. After 6 times washing, proteins associated with beads were released from beads by boiling. Proteins were analyzed by Western blot.

A protocol that was previously reported[46] was used for PMIS pull down. Briefly, miR inhibitor of miR-17 with and without flanking double strand was produced by in vitro transcription. For ARGONAUTE2 and DICER pull down, cell extract of 293FT cell stably expressing PMIS-vector, PMIS-miR-200c or PMIS-miR-17 were incubated with ARGONAUTE2 (Cell Signaling) and DICER (Abcam) antibodies. RNAs were eluted from the pull down complex and primers for PMIS-miR-17 and U6 were used to do RT-PCR.

mRNA Microarray, Correlations of mRNA Fold Change with miR Binding Site

Total RNA was extracted from 293FT cells stably expressing PMIS-vector or PMIS-miR-17. Human Genome microarray hybridization and scan were performed at the Texas A&M University Genomics Core. Microarray data were analyzed with R. Microarray signal intensity were normalized by global median and log 2 transformed. We grouped 22 k mRNA (genes) into three groups, 20 K mRNA without miR-17 binding site (predicted with TargetScan), 2 K mRNA with miR-17 binding site that have context score larger than −0.3 (a score TargetScan used to measure how likely miR can inhibit target mRNA, the lower the score the more likely), another 277 mRNA with miR-17 binding site that have context score less than −0.3. Distribution of mRNA fold change (PMIS-miR-17 vs PMIS-vector) of these three groups was plotted with R using different colors. One-sided K-S test were used to calculate p-value for each pair of comparison between these three groups.

Skeletal Preparations

E18.5 embryos were harvested and placed on ice for 20 minutes, scalded embryos in hot tap water (65° C.) for 30 seconds. After skin removal, embryos were fixed in 95% ethanol overnight. Embryos were incubated in alcian blue solution (0.015% alcian blue 8GX in a 1:4 mixture of acetic acid and 95% ethanol) and alizarin red solution (0.005% alizarin red in 1% KOH) for cartilage and boning staining. Extra tissues were removed in 2% KOH, skeletons were cleared in glycerol-KOH solution (1% KOH, 20% glycerol), and stored in a 1:1 mixture of glycerol and 95% ethanol. Images were captured with a stereo zoom microscope (Nikon SMZ800). The same magnified images were compared between different genotype of embryos.

REFERENCES

1. Ambros, V. The functions of animal microRNAs. *Nature* 431, 350-355 (2004).
2. Bartel, D. P. MicroRNAs: genomics, biogenesis, mechanism, and function. *Cell* 116, 281-297 (2004).
3. He, L. & Hannon, G. J. MicroRNAs: small RNAs with a big role in gene regulation. *Nat. Rev. Genet.* 5, 522-531 (2004).
4. Carthew, R. W. & Sontheimer, E. J. Origins and Mechanisms of miRNAs and siRNAs. *Cell* 136, 642-655 (2009).
5. Bentwich, I. Prediction and validation of microRNAs and their targets. *FEBS Lett* 579, 5904-5910 (2005).

6. Friedman, R. C., Farh, K. K., Burge, C. B. & Bartel, D. P. Most mammalian mRNAs are conserved targets of microRNAs. *Genome Res* 19, 92-105 (2009).
7. Lee, R. C., Feinbaum, R. L. & Ambros, V. The C. elegans heterochronic gene lin-4 encodes small RNAs with antisense complementarity to lin-14. *Cell* 75, 843-854 (1993).
8. Poy, M. N. et al. A pancreatic islet-specific microRNA regulates insulin secretion. *Nature* 432, 226-230 (2004).
9. Brennecke, J., Hipfner, D. R., Stark, A., Russell, R. B. & Cohen, S. M. bantam encodes a developmentally regulated microRNA that controls cell proliferation and regulates the proapoptotic gene hid in Drosophila. *Cell* 113, 25-36 (2003).
10. Cao, H. et al. MicroRNAs play a critical role in tooth development. *J Dent Res* 89, 779-784 (2010).
11. Zhang, Z., Florez, S., Gutierrez-Hartmann, A., Martin, J. F. & Amendt, B. A. MicroRNAs regulate pituitary development, and microRNA 26b specifically targets lymphoid enhancer factor 1 (Lef-1), which modulates pituitary transcription factor 1 (Pit-1) expression. *J Biol Chem* 285, 34718-34728 (2010).
12. Liu, N. & Olson, E. N. MicroRNA regulatory networks in cardiovascular development. *Dev Cell* 18, 510-525 (2010).
13. Cordes, K. R. et al. miR-145 and miR-143 regulate smooth muscle cell fate and plasticity. *Nature* 460, 705-710 (2009).
14. Bartels, C. L. & Tsongalis, G. J. MicroRNAs: novel biomarkers for human cancer. *Clin Chem* 55, 623-631 (2009).
15. Lu, M. et al. An analysis of human microRNA and disease associations. *PLoS One* 3, e3420 (2008).
16. Lu, J. et al. MicroRNA expression profiles classify human cancers. Nature 435, 834-838 (2005). 17. Haraguchi, T. et al. A potent 20-O-methylated RNA-based microRNA inhibitor with unique secondary structures. *Nuc Acid Res.* 40, e58 (2012).
18. Hutvagner, G., Simard, M. J., Mello, C. C. & Zamore, P. D. Sequence-specific inhibition of small RNA function. *PLoS Biol.* 2, E98 (2004).
19. Meister, G., Landthaler, M., Dorsett, Y. & Tuschl, T. Sequence-specific inhibition of microRNA- and siRNA-induced RNA silencing. *RNA* 10, 544-550 (2004).
20. Orom, U. A., Kauppinen, S. & Lund, A. H. LNA-modified oligonucleotides mediate specific inhibition on microRNA function. *Gene* 372, 137-141 (2006).
21. Davis, S., Lollo, B., Freier, S. & Esau, C. Improved targeting of miRNA with antisense oligonucleotides. *Nuc Acid Res.* 34, 2294-2304 (2006).
22. Krutzfeldt, J. et al. Silencing of microRNAs in vivo with 'antagomers'. *Nature* 438, 685-689 (2005).
23. Vermeulen, A. et al. Double-stranded regions are essential design components of potent inhibitors of RISC function. *RNA* 13, 723-730 (2007).
24. Scherr, M. et al. Lentivirus-mediated antagomir expression for specific inhibition of miRNA function. *Nuc. Acid Res.* 35, e149 (2007).
25. Sayed, D. et al. MicroRNA-21 targets Sprouty2 and promotes cellular outgrowths. *Mol. Biol. Cell* 19, 3272-3282 (2008).
26. Ebert, M. S., Neilson, J. R. & Sharp, P. A. MicroRNA sponges: competitive inhibitors of small RNAs in mammalian cells. *Nature Methods* 4, 721-726 (2007).
27. Haraguchi, T., Ozaki, Y. & Iba, H. Vectors expressing efficient RNA decoys achieve the long-term suppression of specific microRNA activity in mammalian cells. *Nuc. Acid Res.* 37, e43 (2009).
28. Davis, S. et al. Potent inhibition of microRNA in vivo without degradation. *Nuc. Acid Res.* 37, 70-77 (2009).
29. Elmén, J. et al. LNA-mediated microRNA silencing in non-human primates. *Nature* 452, 896-899 (2008).
30. Lu, Y. et al. A single anti-microRNA antisense oligodeoxyribonucleotide (AMO) targeting multiple microRNAs offers an improved approach for microRNA interference. *Nuc. Acid Res.* 37, e24 (2009).
31. Hammond, S. M. MicroRNA therapeutics: a new niche for antisense nucleic acids. *TiMM* 12, 99-101 (2006).
32. Cheng, A. M., Byrom, M. W., Shelton, J. & Ford, L. P. Antisense inhibition of human miRNAs and indications for an involvement of miRNA in cell growth and apoptosis. *Nuc. Acid Res.* 33, 1290-1297 (2005).
33. Stenvang, J. & Kauppinen, S. MicroRNAs as targets for antisense-based therapeutics. *Expert Opin. Biol. Ther.* 8, 59-81 (2008).
34. Eckstein, F. The versatility of oligonucleotides as potential therapeutics. *Expert Opin. Biol. Ther.* 7, 1021-1034 (2007).
35. Bartel, D. P. MicroRNAs: target recognition and regulatory functions. *Cell* 136, 215-233 (2009). 36. Ventura, A. et al. Targeted Deletion Reveals Essential and Overlapping Functions of the miR-17-92 Family of miRNA Clusters. *Cell* 132, 875-886 (2008).
37. Gregory, P. A. et al. The miR-200 family and miR-205 regulate epithelial to mesenchymal transition by targeting ZEB1 and SIP1. *Nature Cell Biol.* 10, 593-601 (2008).
38. Gantier, M. P. et al. Analysis of microRNA turnover in mammalian cells following Dicer1 ablation. *Nuc. Acid Res.* 39, 5692-5703 (2011).
39. Wang, J. et al. MicroRNA-17-92, a direct Ap-2a transcriptional target, modulates T-box factor activity in orofacial clefting. *PLoS Genet.* 9, e1003785 (2013).
40. de Pontual, L. et al. Germline deletion of the miR-17~92 cluster causes skeletal and growth defects in humans. *Nat Genet* 43, 1026-1030 (2011).
41. Xie, J. et al. Long-term, efficient inhibition of micro-RNRNA function in mice using rAAV vectors. *Nat. Methods* 9, 403-409 (2012).
42. Gentner, B. et al. Stable knockdown of microRNA in vivo by lentiviral vectors. *Nat. Methods* 6, 63-66 (2009).
43. Zhu, Q. et al. Sponge Transgenic Mouse Model Reveals Important Roles for the MicroRNA-183 (miR-183)/96/182 Cluster in Postmitotic Photoreceptors of the Retina. *J. Biol. Chem.* 286, 31749-31760 (2011).
44. Betancur, J. G. & Tomari, Y. Dicer is dispensable for asymmetric RISC laoding in mammals. *RNA* 18, 24-30 (2012).
45. Donze, O. & Picard, D. RNA interference in mammalian cells using siRNAs synthesized with T7 RNA polymerase. *Nuc. Acids Res.* 30, e46 (2002).
46. Heo, I. et al. TUT4 in Concert with Lin28 Suppresses MicroRNA Biogenesis through Pre-MicroRNA Uridylation. *Cell* 138, 696-708 (2009).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microRNA inhibitor system comprising a nucleic acid vector and at least one expression cassette, wherein each expression cassette comprises a promoter operably linked to a miR inhibitor, wherein the miR inhibitor comprises
   (a) a 5' flanking structure that is 15 to 18 nucleotides in length,
   (b) a 3' flanking structure wherein the 3' flanking structure comprises
      (i) a first 3' stem-loop region comprising a stem of 5 to 8 base pairs in length, and a first loop 8 to 18 nucleotides in length,
      (ii) a single-stranded region,
      (iii) a second stem-loop region; and
      (iv) a region of the 3' flanking structure that forms a double stranded region with the 5' flanking structure, and
   (c) an antisense oligonucleotide (ASO) having a 5' end and a 3' end, wherein the ASO is complementary to a target miR, wherein the ASO comprises a stem-loop region, and wherein the ASO is contiguously linked to the 5' flanking structure at the 5' end of the ASO, and to the 3' flanking structure at the 3' end of the ASO, wherein the 3' flanking structure does not anneal to the ASO, and
   wherein the microRNA inhibitor is about 100 to 135 nucleotides in length.

2. The microRNA inhibitor system of claim 1, wherein the vector is a plasmid or a viral vector.

3. The microRNA inhibitor system of claim 1, wherein the 5' flanking structure is 17 nucleotides in length.

4. The microRNA inhibitor system of claim 1, wherein the first 3' stem-loop region comprises a stem that is 7 basepairs in length.

5. The microRNA inhibitor system of claim 1, wherein the 5' and/or 3' flanking structure independently encode about 50-90% A or U nucleotides.

6. The microRNA inhibitor system of claim 1, wherein 3' flanking structure ends in an A nucleotide.

7. The microRNA inhibitor system of claim 1, wherein the ASO is completely complimentary to a miR and binds with an affinity having a Kd of 100+/−5 nM.

8. The microRNA inhibitor system of claim 1, further comprising a promoter operably linked to a reporter gene.

9. The microRNA inhibitor system of claim 1, wherein the 5' flanking structure is 17 nucleotides in length, wherein the first 3' stem-loop region comprises a stem that is 7 basepairs in length, wherein the 5' and 3' flanking structures independently include about 75-85% AU sequences.

10. A miR inhibitor of about 100 to 135 nucleotides in length, comprising
    (a) a 5' flanking structure that is 15 to 18 nucleotides in length,
    (b) a 3' flanking structure wherein the 3' flanking structure comprises
       (i) a first 3' stem-loop region comprising a stem of 5 to 8 base pairs in length, and a first loop 8 to 18 nucleotides in length,
       (ii) a single-stranded region,
       (iii) a second stem-loop region; and
       (iv) a region of the 3' flanking structure that forms a double stranded region with the 5' flanking structure, and
    (c) an antisense oligonucleotide (ASO) having a 5' end and a 3' end, wherein the ASO is contiguously linked to a 5' flanking structure at the 5' end of the ASO and a 3' flanking structure at the 3' end of the ASO, wherein the ASO comprises a stem-loop region, and wherein, the 3' flanking structure does not anneal to the ASO.

11. The miR inhibitor of claim 10, wherein the 5' and/or 3' flanking structure independently encode about 50-90% A or U nucleotides.

12. The miR inhibitor of claim 10, wherein the ASO is 18 to 26 nucleotides in length.

13. The miR inhibitor of claim 10, wherein 3' flanking structure ends in an A nucleotide.

14. The miR inhibitor of claim 10, wherein the ASO is antisense to a miR and binds with an affinity having a Kd of 100+/−5 nM.

15. The microRNA inhibitor system of claim 1 wherein the system comprises two expression cassettes,
    a first expression cassette comprising a first U6 promoter operably linked to a miR inhibitor that is an antisense oligonucleotide (ASO),
    a second expression cassette comprising a second U6 promoter operably linked to a miR inhibitor that is an antisense oligonucleotide (ASO),
    wherein the 5' flanking structure comprises an antirepressor and
    wherein the 3' flanking structure comprises a scaffold-attached region (SAR) and a polyA site, and
    wherein the 5' flanking structure is operably linked to the first expression cassette and the 3' flanking structure is operably linked to the second expression cassette.

16. The microRNA inhibitor system of claim 1, wherein the 3' flanking structure comprises an overhang at the 3' end.

17. The miR inhibitor of claim 10, wherein the miR inhibitor is associated with RISC complex.

18. The miR inhibitor of claim 10, wherein the 5' flanking structure is encoded by GUCAGCUCUUAGUAUUC (SEQ ID NO: 62).

19. The miR inhibitor of claim 10, wherein the 3' flanking structure is encoded by UCAUAGAGAUCAUAAUCUAUGAACUACAUAGACUUCGGUC AUCUCAUGAAUACUAAGAGCUGACUU (SEQ ID NO: 63).

20. The miR inhibitor of claim 18, wherein the 3' flanking structure is encoded by UCAUAGAGAUCAUAAUCUAUGAACUACAUAGACUUCGGUC AUCUCAUGAAUACUAAGAGCUGACUU (SEQ ID NO: 63).

21. The miR inhibitor of claim 10, wherein the ASO is encoded by UAACUACCUGCACUGUAUCAAAGCACUUUAAUA (SEQ ID NO: 64).

22. The miR inhibitor of claim 10, wherein the inhibitor has the sequence encoded by

```
                                              (SEQ ID NO: 65)
GUCAGCUCUUAGUAUUCUAACUACCUGCACUGUAUCAAAGCACUUUAAUA

UCAUAGAGAUCAUAAUCUAUGAACUACAUAGACUUCGGUCAUCUCAUGAA

UACUAAGAGCUGACUU.
```

* * * * *

UNITED STATES PATENT AND TRADEMARK OFFICE
CERTIFICATE OF CORRECTION

PATENT NO. : 10,519,443 B2
APPLICATION NO. : 15/508857
DATED : December 31, 2019
INVENTOR(S) : Amendt et al.

It is certified that error appears in the above-identified patent and that said Letters Patent is hereby corrected as shown below:

In the Specification

Column 1, Lines 21-23, Statement Regarding Federally Sponsored Research, please delete "This invention was made with the support under DE13941 awarded by the National Institutes of Health. The government has certain rights in the invention." and insert -- This invention was made with government support under DE013941 awarded by the National Institutes of Health. The government has certain rights in the invention. -- therefor.

In the Claims

Column 54, Line 62, please delete "UAUGAACUACAUAGACUUCGGUC AUCU-" and insert -- UAUGAACUACAUAGACUUCGGUCAUCU -- therefor.

Column 54, Line 66, please delete "UAUGAACUACAUAGACUUCGGUC AUCU-" and insert -- UAUGAACUACAUAGACUUCGGUCAUCU -- therefor.

Signed and Sealed this
Third Day of March, 2020

Andrei Iancu
*Director of the United States Patent and Trademark Office*

```
                         SEQUENCE LISTING

<160> NUMBER OF SEQ ID NOS: 65

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 1
caaagugcua acagugcagg uag                                             23

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 2
uaaagugcug acagugcaga u                                               21

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 3
caaagugcuu acagugcagg uag                                             23

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 4
uaaggugcau cuagugcaga uag                                             23
```

```
<210> SEQ ID NO 5
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 5
uaaggugcau cuagugcugu uag                                              23

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 6
ugugcaaauc uaugcaaaac uga                                              23

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 7
aguuuugcag guuugcaucc agc                                              23

<210> SEQ ID NO 8
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 8
aguuuugcag auuugcaguu cagc                                             24

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 9
ugugcaaauc caugcaaaac uga                                              23

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 10
uaaagugcuu auagugcagg uag                                              23
```

```
<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 11
caaagugcuc auagugcagg uag                                               23

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 12
cauugcacuu gucucggucu ga                                                22

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 13
aauugcacgg uauccaucug ua                                                22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 14
cagguggaac acgaugcaau uu                                                22

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 15
agguugggau uugucgcaau gcu                                               23

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 16 aggugggau ugguggcauu ac                                                 22

<210> SEQ ID NO 17
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 17
uauugcacuu gucccggccu g                                              21

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 18
caaagugcug uucgugcagg uag                                            23

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aaggacggug uucuugguca ac                                             22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cugcuugaag cagcucugga uc                                             22

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aggacgacgg caacuacaag ac                                             22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catgtacgtt gctatccagg c                                              21

<210> SEQ ID NO 23
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctccttaatg tcacgcacga t                                           21

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctaatcatca ttaccaatca gacagtatta                                  30

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtcagctctt agtattcatg agatg                                       25

<210> SEQ ID NO 26
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cuaccugcac uguaucaaag cacuuua                                     27

<210> SEQ ID NO 27
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cuaccugcac uguaucaaag cacuuaa                                     27

<210> SEQ ID NO 28
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
cuaccugcac uguaucaaag cacuaua                                     27

<210> SEQ ID NO 29
<211> LENGTH: 27
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 29
cuaccugcac uguaucaaag cacauua                                           27

<210> SEQ ID NO 30
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cuaccugcac uguaucaaag caguuua                                           27

<210> SEQ ID NO 31
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cuaccugcac uguaucaaag cucuuua                                           27

<210> SEQ ID NO 32
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cuaccugcac uguaucaaag gacuuua                                           27

<210> SEQ ID NO 33
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cuaccugcac uguaucaaac cacuuua                                           27

<210> SEQ ID NO 34
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cuaccugcac uguaucaaug cacuuua                                           27

<210> SEQ ID NO 35
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cuaccugcac uguaucauag cacuuua                                         27

<210> SEQ ID NO 36
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cuaccugcac ugaaucaaag cacuuua                                         27

<210> SEQ ID NO 37
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cuaccugcac ucuaucaaag cacuuua                                         27

<210> SEQ ID NO 38
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cuaccugcac aguaucaaag cacuuua                                         27

<210> SEQ ID NO 39
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cuaccugcag uguaucaaag cacuuua                                         27

<210> SEQ ID NO 40
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cuaccugcuc uguaucaaag cacuuua                                         27

<210> SEQ ID NO 41
<211> LENGTH: 27
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 41
cuaccuggac uguaucaaag cacuuua                                              27

<210> SEQ ID NO 42
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cuaccuccac uguaucaaag cacuuua                                              27

<210> SEQ ID NO 43
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cuaccagcac uguaucaaag cacuuua                                              27

<210> SEQ ID NO 44
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cuacgugcac uguaucaaag cacuuua                                              27

<210> SEQ ID NO 45
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cuagcugcac uguaucaaag cacuuua                                              27

<210> SEQ ID NO 46
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cuuccugcac uguaucaaag cacuuua                                              27

<210> SEQ ID NO 47
<211> LENGTH: 27
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 47
caaccugcac uguaucaaag cacuuua                27

<210> SEQ ID NO 48
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
guaccugcac uguaucaaag cacuuua                27

<210> SEQ ID NO 49
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuaccugcac uguaucaaac cacuuaa                27

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uaacacuguc ugguaacgau gu                     22

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaacacuguc ugguaaagau gg                     22

<210> SEQ ID NO 52
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uaauacugcc ugguaaugau ga                     22

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 53
uaauacugcc ggguaaugau gga                                              23

<210> SEQ ID NO 54
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uaauacuguc ugguaaaacc gu                                               22

<210> SEQ ID NO 55
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
caaagugcuu acagugcagg uagu                                             24

<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
caaagugcuc auagugcagg ua                                               22

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
caaagugcua acagugcagg ua                                               22

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uaaggugcau cuagugcaga ua                                               22

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 59
uaaggugcau cuagugcagu ua                                              22

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aauugcacgg uauccaucug uaa                                             23

<210> SEQ ID NO 61
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 61
gucagcucuu aguauucuaa cuaccugcac uguaucaaag cacuuuaaua ucauagagau      60
cauaaucuau gaacuacaua gacuucgguc aucucaugaa uacuaagagc ugacuu        116

<210> SEQ ID NO 62
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gucagcucuu aguauuc                                                    17

<210> SEQ ID NO 63
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ucauagagau cauaaucuau gaacuacaua gacuucgguc aucucaugaa uacuaagagc      60
ugacuu                                                                66

<210> SEQ ID NO 64
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uaacuaccug cacuguauca aagcacuuua aua                                  33

<210> SEQ ID NO 65
<211> LENGTH: 116
<212> TYPE: RNA
<213> ORGANISM: Artificial Sequence
<220> FEATURE:
```

-continued

```
<223> OTHER INFORMATION: Description of Artificial Sequence: Synthetic
      polynucleotide

<400> SEQUENCE: 65
gucagcucuu aguauucuaa cuaccugcac uguaucaaag cacuuuaaua ucauagagau      60
cauaaucuau gaacuacaua gacuucgguc aucucaugaa uacuaagagc ugacuu        116
```